(12) United States Patent
Traynelis et al.

(10) Patent No.: US 7,375,136 B2
(45) Date of Patent: May 20, 2008

(54) PH-DEPENDENT NMDA RECEPTOR ANTAGONISTS

(75) Inventors: Stephen F. Traynelis, Decatur, GA (US); Dennis C. Liotta, Atlanta, GA (US); James P. Snyder, Atlanta, GA (US); Yesim Altas, Decatur, GA (US); David D. Mott, Tucker, GA (US); James J. Doherty, Jr., Landenberg, PA (US); Raymond J. Dingledine, Atlanta, GA (US)

(73) Assignee: Emory University, Atlanta, GA (US)

( * ) Notice: Subject to any disclaimer, the term of this patent is extended or adjusted under 35 U.S.C. 154(b) by 148 days.

(21) Appl. No.: 10/469,824

(22) PCT Filed: Mar. 8, 2002

(86) PCT No.: PCT/US02/07033

§ 371 (c)(1),
(2), (4) Date: Feb. 25, 2004

(87) PCT Pub. No.: WO02/072542

PCT Pub. Date: Sep. 19, 2002

(65) Prior Publication Data

US 2004/0138502 A1    Jul. 15, 2004

Related U.S. Application Data

(60) Provisional application No. 60/274,205, filed on Mar. 8, 2001.

(51) Int. Cl.
*A61K 31/18* (2006.01)
*C07C 311/18* (2006.01)

(52) U.S. Cl. .................................. 514/605; 564/99

(58) Field of Classification Search .............. 564/99; 514/605
See application file for complete search history.

(56) References Cited

U.S. PATENT DOCUMENTS

| | | | |
|---|---|---|---|
| 4,906,779 A | 3/1990 | Weber et al. |
| 4,924,008 A | 5/1990 | Abou-Gharbia et al. |
| 4,957,909 A | 9/1990 | Abou-Gharbia et al. |
| 4,959,366 A | 9/1990 | Cross et al. |
| 4,994,467 A | 2/1991 | Zimmerman |
| 5,013,540 A | 5/1991 | Redburn |
| 5,034,400 A | 7/1991 | Olney |
| 5,039,528 A | 8/1991 | Olney |
| 5,093,525 A | 3/1992 | Weber |
| 5,095,009 A | 3/1992 | Whitten |
| 5,106,847 A | 4/1992 | Salituro |
| 5,118,675 A | 6/1992 | Jirkovsky |
| 5,124,319 A | 6/1992 | Baudy |
| 5,132,313 A | 7/1992 | Kozikowski |
| 5,179,085 A | 1/1993 | Bigge |
| 5,189,054 A | 2/1993 | Salituro |
| 5,190,976 A | 3/1993 | Weber |
| 5,192,751 A | 3/1993 | Thor |
| 5,194,430 A | 3/1993 | Whitten |
| 5,262,568 A | 11/1993 | Weber |
| 5,318,985 A | 6/1994 | McDonald |
| 5,321,012 A | 6/1994 | Mayer |
| 5,326,756 A | 7/1994 | Whitten |
| 5,336,689 A | 8/1994 | Weber |
| 5,385,903 A | 1/1995 | Steppuhn |
| 5,385,947 A | 1/1995 | Godel |
| 5,395,822 A | 3/1995 | Izumi |
| 5,441,963 A | 8/1995 | McDonald |
| 5,470,844 A | 11/1995 | Whitten |
| 5,474,990 A | 12/1995 | Olney |
| 5,489,579 A | 2/1996 | McDonald |
| 5,491,153 A | 2/1996 | Salituro |
| 5,498,610 A | 3/1996 | Chenard |
| 5,502,058 A | 3/1996 | Mayer |
| 5,519,048 A | 5/1996 | Salituro |

(Continued)

FOREIGN PATENT DOCUMENTS

| | | | |
|---|---|---|---|
| WO | 91/13865 | * | 9/1991 |
| WO | WO 91/13865 A1 | | 9/1991 |
| WO | WO 01/02406 | * | 1/2001 |

OTHER PUBLICATIONS

Connors et al., Chem. Abst. 114:228481.*
Alanine, A. et al., "1-benzyloxy-4,5-dihydro-1H-imidzzol-2-yl-amines, a novel class of NR1/2B subtype selective NMDA receptor antagonists," Bioorganic & Medicinal Chemistry Letters 13:3155-3159, 2003.
Bradford, H. R., "Glutamate, GABA, and epilepsy," Progress in Neurobiology 47:477-511, 1995.
Choi, D., "Antagonizing excitotoxicity: A therapeutic strategy for stroke?" Mount Sinai J. Med. 65(2):133-138, 1998.

(Continued)

*Primary Examiner*—Peter O'Sullivan
(74) *Attorney, Agent, or Firm*—King & Spalding

(57) ABSTRACT

NMDA receptor blockers, including pH-sensitive NMDA receptor blockers, are provided as neuroprotective drugs that are useful in stroke, traumatic brain injury, epilepsy, and other neurologic events that involve acidification of brain or spinal cord tissue. Compositions and methods of this invention are used for treating neurodegeneration resulting from NMDA receptor activation. The compounds described herein have enhanced activity in brain tissue having lower-than normal pH due to pathological conditions such as hypoxia resulting from stroke, traumatic brain injury, global ischemia that may occur during cardiac surgery, hypoxia that may occur following cessation of breathing, pre-eclampsia, spinal cord trauma, epilepsy, chronic pain, vascular dementia and glioma tumors. Compounds described herein are also useful in preventing neurodegeneration in patients with Parkinson's Alzheimer's, Huntington's chorea, ALS, and other neurodegenerative conditions known to the art to be responsive to treatment using NMDA receptor blockers. Preferably the compounds provided herein are allosteric NMDA inhibitors.

8 Claims, No Drawings

U.S. PATENT DOCUMENTS

| | | | |
|---|---|---|---|
| 5,538,958 A | 7/1996 | Whitten | |
| 5,556,838 A | 9/1996 | Mayer | |
| 5,559,154 A | 9/1996 | Weber | |
| 5,563,157 A | 10/1996 | Harrison | |
| 5,587,384 A | 12/1996 | Zhang | |
| 5,594,007 A | 1/1997 | Chenard | |
| 5,605,911 A | 2/1997 | Olney | |
| 5,606,063 A | 2/1997 | Harrison | |
| 5,614,509 A | 3/1997 | Turski | |
| 5,616,580 A | 4/1997 | Olney | |
| 5,629,307 A | 5/1997 | Olney | |
| 5,633,379 A | 5/1997 | Allgeier | |
| 5,637,622 A | 6/1997 | Weber | |
| 5,654,281 A | 8/1997 | Mayer | |
| 5,675,018 A | 10/1997 | Salituro | |
| 5,703,107 A | 12/1997 | Salituro | |
| 5,710,139 A | 1/1998 | Swahn | |
| 5,710,168 A | 1/1998 | Chenard | |
| 5,714,500 A | 2/1998 | Griffith | |
| 5,753,657 A | 5/1998 | Aloup | |
| 5,767,130 A | 6/1998 | Olney | |
| 5,767,162 A | 6/1998 | Weber | |
| 5,777,114 A | 7/1998 | Aloup | |
| 5,783,572 A | 7/1998 | Mowbray | |
| 5,783,700 A | 7/1998 | Nichols | |
| 5,798,390 A | 8/1998 | Weber | |
| 5,834,465 A | 11/1998 | Olney | |
| 5,834,479 A | 11/1998 | Mayer | |
| 5,840,731 A | 11/1998 | Mayer | |
| 5,863,922 A | 1/1999 | Mayer | |
| 5,866,585 A | 2/1999 | Fogel | |
| 5,869,498 A | 2/1999 | Mayer | |
| 5,888,996 A | 3/1999 | Farb | |
| 5,889,026 A | 3/1999 | Alanine | |
| 5,902,815 A | 5/1999 | Olney | |
| 5,919,826 A | 7/1999 | Caruso | |
| 5,922,716 A | 7/1999 | Aloup | |
| 5,925,634 A | 7/1999 | Olney | |
| 5,952,344 A | 9/1999 | Alanine | |
| 5,958,919 A | 9/1999 | Olney | |
| 5,962,472 A | 10/1999 | Bourson | |
| RE36,397 E | 11/1999 | Zhang | |
| 5,981,553 A | 11/1999 | Farr | |
| 5,990,126 A | 11/1999 | Park | |
| 6,007,841 A | 12/1999 | Caruso | |
| 6,025,369 A | 2/2000 | Rosenquist | |
| 6,034,134 A | 3/2000 | Gold | |
| 6,054,451 A | 4/2000 | Caruso | |
| 6,057,358 A * | 5/2000 | Chung et al. | 514/427 |
| 6,057,373 A | 5/2000 | Fogel | |
| 6,071,929 A | 6/2000 | Alanine | |
| 6,071,966 A | 6/2000 | Gold | |
| 6,080,743 A | 6/2000 | Acklin | |
| 6,083,941 A | 7/2000 | Farb | |
| 6,096,743 A | 8/2000 | Shishikura | |
| 6,177,434 B1 | 1/2001 | Kopke | |
| 6,180,786 B1 | 1/2001 | Metz, Jr. | |
| 6,184,236 B1 * | 2/2001 | Alanine et al. | 514/329 |
| 6,187,338 B1 | 2/2001 | Caruso | |
| 6,194,000 B1 | 2/2001 | Smith | |
| 6,197,820 B1 | 3/2001 | Sontheimer | |
| 6,200,990 B1 | 3/2001 | Namil | |
| 6,242,456 B1 | 6/2001 | Shuster | |
| 6,251,948 B1 | 6/2001 | Weber | |
| 6,258,827 B1 | 7/2001 | Chenard | |
| 6,265,426 B1 | 7/2001 | Alanine | |
| 6,274,633 B1 | 8/2001 | Franks | |
| 6,284,774 B1 | 9/2001 | Wright | |
| 6,284,776 B1 | 9/2001 | Meltzer | |
| 6,294,583 B1 | 9/2001 | Fogel | |
| 6,339,093 B1 | 1/2002 | Alanine | |

OTHER PUBLICATIONS

Claiborne, C. F. et al., "Orally efficacious NR2B-selective NMDA receptor antagonists," Bioorganic & Medicinal Chemistry Letters 13:697-700, 2003.

Curtis, N. R., "Novel $N^1$-(benzyl)dinnamamidine derived NR2B subtype-selective NMDA receptor antagonists," Bioorganic & Medicinal Chemistry Letters 13:693-696, 2003.

Dingledine, R. et al., "The glutamate receptor ion channels," Pharmacological Reviews 51(1):7-61, 1999.

Dirnagl, U. et al., "Pathobiology of ischaemic stroke: An integrated view," TINS 22(9):391-397, 1999.

McNamara, J. O., "Drugs effective in the therapy of the epilepsies," Chapter 21 In Goodman & Gliman's: *The Pharmacological Basis of Therapeutics*, J. G. Hardman and L. E. Limbird (eds.), McGraw Hill, New York, pp. 521-547, 2001.

Mott, D. D. et al., "Phenylethanolamines inhibit NMDA receptors by enhancing proton inhibition," Nature Neuroscience 1(8):659-667, 1998.

Muir, K. W. et al., "Clinical experience with excitatory amino acid antagonist drugs," Stroke 26:503-513, 1995.

Obrenovitch, T. P. et al., "Is high extracellular glutamate the key to excitotoxicity in traumatic brain injury?" J. Neurotrauma 14(10):677-698, 1997.

Rothstein, J. D. et al., "Excitotoxic destruction facilitates brain tumor growth," Nature Medicine 7(9):994-995, 2001.

Rzeski, W. et al., "Glutamate antagonists limit tumor growth," Proc. Natl. Acad. Sci. 98(11):6372-6377, 2001.

Takano, T. et al., "Glutamate release promotes growth of malignant gliomas," Nature Medicine 7(9):1010-1015, 2001.

Traynelis, S. F. et al., "Proton inhibition of N-methyl-D-aspartate receptors in cerebellar neurons," Nature 345:347-350, 1990.

Traynelis, S. F. et al., "Control of proton sensitivity of the NMDA receptor by RNA splicing and polyamines," Science 268:873-876, 1995.

International Search Report of International Application No. PCT/US02/07053, date of mailing Sep. 11, 2002, 2 pages.

* cited by examiner

PH-DEPENDENT NMDA RECEPTOR ANTAGONISTS

CROSS-REFERENCE TO RELATED APPLICATIONS

This application is a 371 of PCT/US02/07033, filed 8 Mar. 2002 which claims the benefit of U.S. patent application Ser. No. 60/274,205, filed Mar. 8, 2001, which is incorporated herein by reference to the extent not inconsistent herewith.

BACKGROUND

NMDA receptors are a subtype of glutamate-gated ion channels that mediate excitatory synaptic transmission between neurons in the central nervous system (Dingledine, R. et al., [1999], "The glutamate receptor ion channels," *Pharmacological Reviews* 51:7-61). NMDA receptors are a subtype of the most widespread excitatory neurotransmitter receptor in the brain. Excessive activation of NMDA receptors kills neurons, and current evidence implicates NMDA receptor activation in a variety of neurologic disorders that include epilepsy, ischemic brain damage, traumatic brain/spinal cord injury, and Alzheimer's Diseases, Huntington's chorea and Amyotrophic Lateral Sclerosis (ALS).

In animal models of stroke and brain trauma, glutamate released from affected neurons can overstimulate NMDA receptors, which in turn causes neuronal death. Because overactivation of NMDA receptors is neurotoxic, compounds that block NMDA receptors have been considered candidates for treatment of stroke or head injuries. Numerous animal studies have validated NMDA receptors as targets for neuroprotection in stroke, brain and spinal cord trauma, and related settings that involve brain ischemia. NMDA receptor blockers are effective in limiting the volume of damaged brain tissue in experimental models of stroke and traumatic brain injury. (Choi, D. (1998), "Antagonizing excitotoxicity: A therapeutic strategy for stroke," *Mount Sinai J. Med*. 65:133-138; Dirnagle, U. et al. (1999) "Pathobiology of ischaemic stroke: an integrated view," *Tr. Neurosci*. 22:391-397; Obrenovitch, T. P. and Urenjak, J. (1997) "Is high extracellular glutamate the key to excitotoxicity in traumatic brain injury," *J. Neurctrauma* 14:677-698.) In addition, NMDA receptor antagonists are known to be anti-convulsant in many experimental models of epilepsy (Bradford, H. R. [1995] "Glutamate, GABA, and Epilepsy," *Progress in Neurobiology* 47:477-511; McNamara, J. O. [2001] Drugs effective in the therapy of the epilepsies. In Goodman & Gliman's: The pharmacological basis of therapeutics [Eds. J. G. Hardman and L. E. Limbird] McGraw Hill, New York). However, dose-limiting side effects have thus far prevented clinical use of NMDA receptor antagonists for these neurologic conditions (Muir, K. W. and Lees, K. R. [1995] "Clinical experience with excitatory amino acid antagonist drugs," *Stroke* 26:503-513; Herrling, P. L., ed. [1997] "Excitatory amino acid—clinical results with antagonists" Academic Press; Parsons, C. G. et al. [1998] "Glutamate in CNS disorders as a target for drug development: an update," *Drug News Perspective* 11:523-569), and consequently enthusiasm for this receptor protein as a drug target has diminished within the pharmaceutical industry. NMDA receptor blockers also act synergistically with L-DOPA to relieve symptoms of Parkinsonism. In addition, such compounds are useful for treating chronic neuropathic pain and bipolar disorder. However, the first three generations of NMDA receptor antagonists (channel blockers, competitive blockers of the glutamate or glycine agonist sites, and noncompetitive allosteric antagonists) have not proved useful clinically.

Several recent papers have suggested that rapidly-growing brain gliomas can kill adjacent neurons by secreting glutamate and overactivating NMDA receptors The dying neurons make room for the growing tumor, and may release cellular components that stimulate tumor growth. These studies shown NMDA receptor antagonists can reduce the rate of tumor growth in vivo as well as in some in vitro models. (Takano, T., et al. (2001), "Glutamate release promotes growth of malignant glioma," Nature Medicine 7:1010-1015; Rothstein, J. D. and Bren, H. (2001), "Excitotoxic destruction facilitates brain tumor growth," Nature Medicine 7:994-995; Rzeski, W., et al. (2001), "Glutamate antagonists limit tumor growth," Proc. Nat'l Acad. Sci 98:6372-6377.)

In the late 1980's a new class of NMDA receptor antagonists (phenylethanolamines) was discovered which did not bind at the agonist binding sites. This class, exemplified by the compound ifenprodil, selectively interacts with NMDA receptors containing the NR2B subunit. These compounds have exhibited neuroprotective properties in preclinical models. This class of antagonist lacks the severe side-effect liability of other types of NMDA antagonists (e.g. PCP-like psychotic symptoms and cardiovascular effects).

One of the most prevalent subtypes of NMDA receptor which contains the NR2B subunit has the unusual property of being normally inhibited by protons by about 50% at physiological pH (Traynelis, S. F. and Cull-Candy, S. G. [1990] "Proton inhibition of N-methyl-D-aspartate receptors in cerebellar neurons," *Nature* 345:347-350. We have found that phenylethanolamines, typified by ifenprodil and CP101, 606 inhibit activation of NMDA receptors by potentiating allosteric inhibition mediated by protons. In turn, small reduction of pH in the physiological range increases the potency of some phenylethanol-amines as NMDA receptor antagonists. The potency of ifenprodil for inhibition of NR2B subunit-containing recombinant NMDA receptors is enhanced at pH 6.8 compared to pH 7.5. (Mott et al. [1998], "Phenylethanolamines inhibit NMDA receptors by enhancing proton inhibition," Nature Neuroscience 1(8):659-667.) Ischemic brain tissue, as well as the site of seizure generation in epilepsy, is characterized by a lower pH than is found in brain tissue.

Therapeutic compounds for the foregoing pathologies may have toxic side effects. It is thus an object of this invention to provide compounds which have enhanced activity under the lower pH conditions characteristic of such pathologies, and which are less active under the normal pH conditions of healthy brain tissue.

A number of patents discuss NMDA receptor antagonists, including U.S. Pat. No. 6,080,743 to Acklin et al.; U.S. Pat. Nos. 4,924,008 and 4,957,909 to Abou-Gharbia et al.; U.S. Pat. Nos. 5,889,026, 5,952,344, 6,071,929, 6,265,426, and 6,339,093 to Alanine et al.; U.S. Pat. No. 5,633,379 to Allgeier; U.S. Pat. Nos. 5,922,716, 5,753,657 and 5,777,114 to Aloup et al.; U.S. Pat. No. 5,124,319 to Baudy et al.; U.S. Pat. No. 5,179,085 to Bigge et al.; U.S. Pat. No. 5,962,472 to Bourson et al.; U.S. Pat. Nos. 5,919,826, 6,007,841, 6,054,451, and 6,187,338 to Caruso et al.; U.S. Pat. Nos. 5,498,610, 5,594,007, 5,710,168, and 6,258,827 to Chenard et al.; U.S. Pat. Nos. 5,888,996 and 6,083,941 to Farb; U.S. Pat. No. 5,981,553 to Farr et al.; U.S. Pat. Nos. 5,866,585, 6,057,373, and 6,294,583 to Fogel; U.S. Pat. No. 6,274,633 to Franks et al.; U.S. Pat. No. 5,385,947 to Godel et al.; U.S. Pat. No. 6,034,134 and 6,071,966 to Gold et al.; U.S. Pat.

No. 5,714,500 to Griffith et al.; U.S. Pat. Nos. 5,563,157 and 5,606,063 to Harrison et al.; U.S. Pat. No. 5,395,822 to Izumi et al.; U.S. Pat. No. 5,118,675 to Jirkovsky et al.; U.S. Pat. No. 6,177,434 to Kopke et al.; U.S. Pat. No. 5,132,313 to Kozikowski et al.; U.S. Pat. Nos. 5,321,012, 5,502,058, 5,556,838, 5,654,281, 5,834,479, 5,840,731, 5,863,922, and 5,869,498 to Mayer et al.; U.S. Pat. Nos. 5,318,985, 5,441,963 and 5,489,579 to McDonald et al.; U.S. Pat. No. 6,284,776 to Meltzer; U.S. Pat. No. 6,180,786 to Metz, Jr.; U.S. Pat. No. 5,783,572 to Mowbray et al.; U.S. Pat. No. 6,200,990 to Namil et al.; U.S. Pat. No. 5,783,700 to Nichols et al.; U.S. Pat. Nos. 5,034,400, 5,039,528, 5,474,990, 5,605,911, 5,616,580, 5,629,307, 5,767,130, 5,834,465, 5,902,815, 5,925,634, and 5,958,919 to Olney et al.; U.S. Pat. No. 5,990,126 to Park et al.; U.S. Pat. No. 5,013,540 to Redburn; U.S. Pat. No. 6,025,369 to Rosenquist et al.; U.S. Pat. Nos. 5,106,847, 5,189,054 5,491,153, 5,519,048 5,675,018, and 5,703,107 to Salituro et al.; U.S. Pat. No. 6,096,743 to Shishikura et al.; U.S. Pat. No. 6,242,456 to Shuster et al.; U.S. Pat. No. 6,194,00 to Smith et al.; U.S. Pat. No. 6,197,820 to Sontheimer et al.; U.S. Pat. No. 5,385,903 to Steppuhn et al.; U.S Pat. No. 5,710,139 to Swahn; U.S. Pat. No. 5,192,751 to Thor; U.S. Pat. No. 5,614,509 to Turski et al.; U.S. Pat. Nos. 4,906,779, 5,093,525, 5,190,976, 5,262,568, 5,336,689, 5,559,154, 5,637,622, 5,767,162, 5,798,390, and 6,251,948 to Weber et al.; U.S. Pat. Nos. 5,095,009 5,194,430, 5,326,756, 5,470,844, and 5,538,958 to Whitten; U.S. Pat. No. 6,284,774 to Wright et al.; U.S. Pat. Nos. 5,587,384 and Re 36,397 to Zhang et al.; and U.S. Pat. No. 4,994,467 to Zimmerman. However, NMDA receptor blockers are needed which are enhanced at low pHs characteristic of certain pathological conditions for treatment of such pathological conditions.

All publications referred to herein are incorporated by reference to the extent not inconsistent herewith.

SUMMARY

This invention provides NMDA receptor blockers, including pH-sensitive NMDA receptor blockers, as neuroprotective drugs that are useful in stroke, traumatic brain injury, epilepsy, and other neurologic events that involve acidification of brain or spinal cord tissue. Compositions and methods of this invention are used for treating neurodegeneration resulting from NMDA receptor activation. The compounds described herein have enhanced activity in brain tissue having lower-than-normal pH due to pathological conditions such as hypoxia resulting from stroke, traumatic brain injury, global ischemia that may occur during cardiac surgery, hypoxia that may occur following cessation of breathing, pre-eclampsia, spinal cord trauma, epilepsy, status epilepticus, neuropathic or inflammatory pain, chronic pain, vascular dementia and glioma tumors. Because tumors produce an acidic environment, drugs activated by low pH are useful in slowing tumor growth because they have enhanced activity only at the site of the tumor. Compounds described herein are also useful in preventing neurodegeneration in patients with Parkinson's Alzheimer's, Huntington's chorea, ALS, and other neurodegenerative conditions known to the art to be responsive to treatment using NMDA receptor blockers. Preferably the compounds provided herein are allosteric NMDA inhibitors.

Also preferably, the compounds provided herein are selective NMDA receptor blockers, that is, they do not interact with other receptors or ion channels at therapeutic concentrations. General blocking of NMDA receptors throughout the brain causes adverse effects such as ataxia, memory deficits, hallucinations and other neurological problems.

The compounds provided herein block the NR2B-containing NMDA receptors, have varying activity against receptors containing NR2A or NR2D, and may be selective for other members of the NMDA receptor family (NR2C, NR3A and NR3B).

The novel small molecule NMDA receptor antagonists of this invention are useful both in the treatment of stroke and head trauma in the emergency room setting, and for use as prophylactic agents for at risk patients. The acid generated by ischemic tissue during stroke is harnessed as a switch to activate the neuroprotective agents described herein. In this way side effects are minimized in unaffected tissue since drug at these sites are less active. These compounds reduce the amount of neuronal death associated with stroke and head trauma. These compounds also have military uses as a neuroprotective for battlefield head trauma. They may be given chronically to individuals with epilepsy or who are at risk for stroke or head trauma, preoperatively in high risk heart/brain surgery, etc., in order to lengthen the window of opportunity for subsequent therapy.

This invention provides the following useful for treating conditions characterized by lowered brain-tissue pH, selected from the group consisting of (R)- and (S)-enantiomers and mixtures thereof of compounds of the formula:

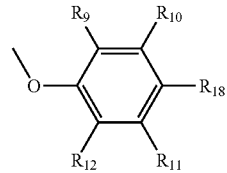

A-B- wherein one of $R_9$, $R_{10}$, $R_{11}$, $R_{12}$ and $R_{18}$ is

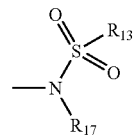

where $R_{13}$ is alkyl, aralkyl or aryl; where $R_{17}$ is H or lower alkyl; and the others of $R_9$, $R_{10}$, $R_{11}$, $R_{12}$ and $R_{18}$ are H, F, Cl, I or R wherein R is lower alkyl; or:

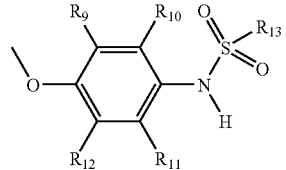

A-B- wherein $R_9$, $R_{10}$, $R_{11}$, and $R_{12}$ are independently selected from the group consisting of H, F, Cl, Br, I, and R wherein R is lower alkyl, and $R_{13}$ is alkyl aralkyl or aryl;

wherein A is selected from the group consisting of:

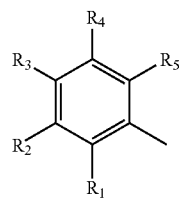

wherein $R_1$ and $R_5$ are independently H or F; $R_2$, $R_3$ and $R_4$ are independently selected from the group consisting of H, F, Cl, Br, I and OR where R is lower alkyl, or $R_2$ and $R_3$ taken together are O—CH$_2$—O;

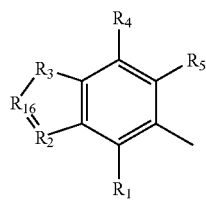

wherein $R_1$, $R_4$, and $R_5$ are independently selected from the group consisting of H, F, Cl, Br, I and OR where R is lower alkyl, $R_3$ is independently O, S, NH or NR, $R_2$ is N, and $R_{16}$ is C-alkyl, C-aralkyl or C-aryl;

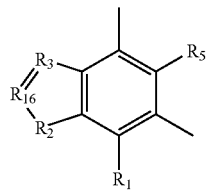

wherein $R_1$, $R_4$, and $R_5$ are independently selected from the group consisting of H, F, Cl, Br, I and OR where R is lower alkyl, $R_2$ is independently O, S, NH or NR, $R_3$ is N; and $R_{16}$ is C-alkyl, C-aralkyl or C-aryl;

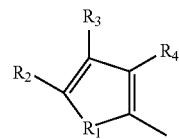

wherein $R_1$ through $R_4$ are independently selected from the group consisting of H, F, Cl, Br, I and OR where R is lower alkyl, or $R_2$ and $R_3$ taken together are O—CH$_2$—O;

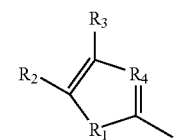

wherein $R_1$, $R_2$ and $R_3$ are independently selected from the group consisting of O, S, NH or NR where R is lower alkyl, or $R_2$ and $R_3$ taken together are O—CH$_2$—O, and $R_4$ is N;

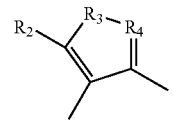

wherein $R_2$ and $R_3$ are independently selected from the group consisting of H, F, Cl, Br, I and OR where R is lower alkyl; and $R_4$ is N;

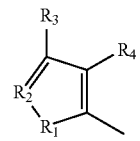

wherein $R_1$ is selected from the group consisting of O, S, NH and NR where R is lower alkyl; $R_2$ is N, and $R_3$ and R are independently selected from the group consisting of H, F, Cl, Br, I and OR where R is lower alkyl;

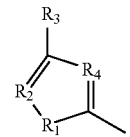

wherein $R_1$ is selected from the group consisting of O, S, NH and NR where R is lower alkyl; $R_2$ and $R_4$ are N, and $R_3$ is independently selected from the group consisting of H, F, Cl, Br, I and OR where R is lower alkyl;

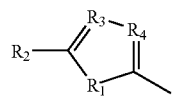

wherein $R_1$ is selected from the group consisting of O, S, NH and NR where R is lower alkyl; $R_2$ is selected from the group consisting of H, F, Cl, Br, I and OR where R is lower alkyl; and $R_3$ and $R_4$ are N;

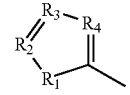

wherein $R_1$ is selected from the group consisting of O, S, NH and NR where R is lower alkyl; and $R_2$, $R_3$ and $R_4$ are N;

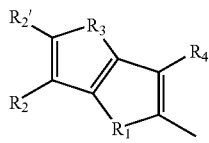

wherein $R_1$ and $R_3$ are independently selected from the group consisting of O, S, NH and NR where R is lower alkyl; and $R_2$, $R_2'$ and $R_4$ are independently selected from the group consisting of H, F, Cl, Br, I and OR where R is lower alkyl;

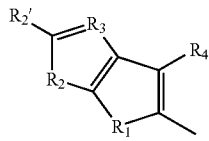

wherein $R_1$ and R2 are independently selected from the group consisting of O, S, NH and NR where R is lower alkyl; and $R_2'$, and $R_3$ and R4 are independently selected from the group consisting of H, F, Cl, Br, I and OR where R is lower alkyl;

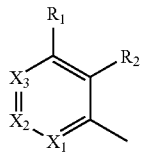

wherein $X_1$ is C—$R_3$ or N, $X_2$ is C—$R_4$ or N, $X_3$ is C—$R_4'$ or N where $R_1$—$R_4'$ are independently selected from the group consisting of O, S, NH and NR where R is lower alkyl, or where $R_1$ and $R_2$ taken together are O—$CH_2$—O;

and wherein B is selected from the group consisting of:

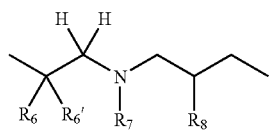

wherein $R_6$ and $R_6'$ are independently H or F; and $R_7$ is H, lower n-alkyl, $CH_2Ar$, $CH_2CH_2Ar$, $CH_2CHFAr$, or $CH_2CHF_2Ar$; and $R_8$ is OH, OR, where R is lower alkyl, or F;

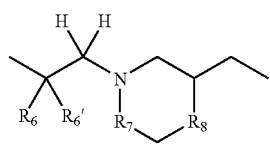

wherein $R_6$ and $R_6'$ are independently H or F; $R_7$ is $CH_2$ and $R_8$ is O;

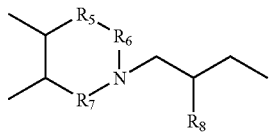

wherein $R_5$, $R_6$ and $R_7$ are independently $CH_2$, CHR or $CR_2$ where R is lower alkyl; and $R_8$ is OH, OR, where R is lower alkyl, or F;

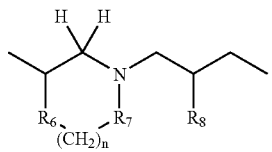

wherein $R_6$ and $R_7$ are independently $CH_2$, CHR or $CR_2$ where R is lower alkyl; and $R_8$ is OH, OR, where R is lower alkyl, or F;

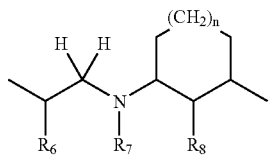

wherein $R_6$ and $R_7$ are independently $CH_2$, CHR or CR2 where R is lower alkyl; $R_8$ is OH or F; and n=1-3; and pharmaceutically acceptable salts, enantiomers, enantiomeric mixtures, and mixtures of the foregoing.

These compounds are preferably provided in combination with a suitable pharmaceutical carrier.

Preferred compounds of this invention include (R)- and (S)-enantiomers and mixtures thereof of compounds selected from the group consisting of:

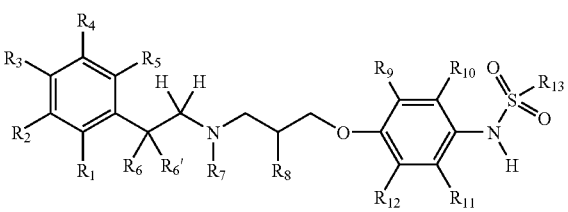

wherein $R_1$ and $R_5$ are independently H or F; and
when $R_1$ and $R_5$ are H, $R_2$, $R_3$ and $R_4$ are independently selected from the group consisting of H, F, Cl, Br, I and OR where R is lower alkyl, and $R_2$ and $R_3$ taken together are O—$CH_2$—O; $R_6$ and $R_6'$ are independently H or F; $R_7$ is selected from the group consisting of lower n-alkyl, $CH_2Ar$, $CH_2CH_2Ar$, $CH_2CHFAr$ and $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br I and lower alkyl; and $R_{13}$ is alkyl, aralkyl or aryl; and when one of $R_1$ or $R_5$ is F and the other is H or F, $R_2$, $R_3$ and $R_4$ are independently selected from the group consisting of H, F, Cl, Br, I and OR where R is lower alkyl and $R_2$ and $R_3$ taken together are O—CH$_2$—O; $R_6$ and $R_6'$ are independently H or F; $R_7$ is selected from the group consisting of H, lower n-alkyl, CH$_2$Ar, CH$_2$CH$_2$Ar, CH$_2$CHFAr and CH$_2$CF$_2$Ar, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br I and lower alkyl; and $R_{13}$ is alkyl, aralkyl or aryl;

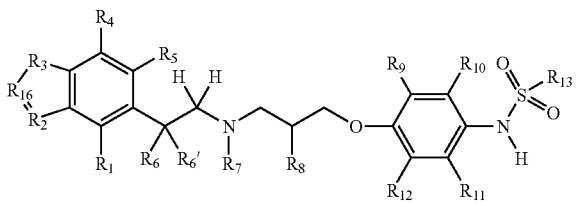

wherein $R_1$ and $R_5$ are independently H or F; $R_2$ is N; $R_3$ is O, S, NH or NR where R is lower alkyl; $R_4$ is selected from the group consisting of H, F, Cl, Br, I and OR where R is lower alkyl, $R_6$ and $R_6'$ are independently H or F; $R_7$ is selected from the group consisting of H, lower n-alkyl, CH$_2$Ar, CH$_2$CH$_2$Ar, CH$_2$CHFAr and CH$_2$CF$_2$Ar, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br I and lower alkyl; $R_{13}$ is alkyl, aralkyl or aryl; and $R_{16}$ is C-alkyl, C-aralkyl or C-aryl;

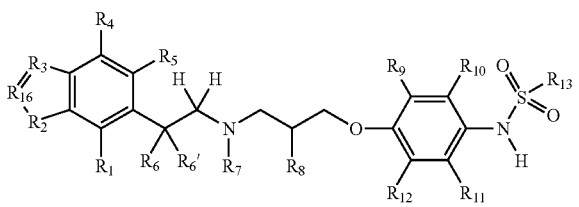

wherein $R_1$ and $R_5$ are independently H or F; $R_2$ is independently O, S, NH or NR where R is lower alkyl; $R_3$ is N; $R_4$ is selected from the group consisting of H, F, Cl, Br, I and OR wherein R is lower alkyl, $R_6$ and $R_6'$ are independently H or F; $R_7$ is selected from the group consisting of H, lower n-alkyl, CH$_2$Ar, CH$_2$CH$_2$Ar, CH$_2$CHFAr and CH$_2$CF$_2$Ar, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br I and lower alkyl; $R_{13}$ is alkyl, aralkyl or aryl; and $R_{16}$ is C-alkyl, C-aralkyl, or C-aryl;

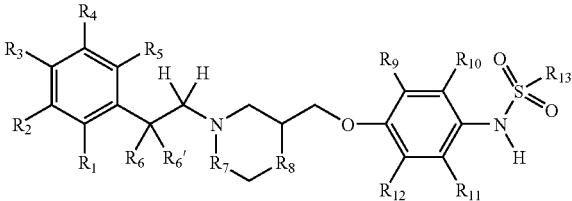

wherein $R_1$ through $R_5$ are independently selected from the group consisting of H, F, Cl, Br, I and OR$_{14}$, and $R_2$ and $R_3$ taken together are O—CH$_2$—O; $R_6$ and $R_6'$ are independently H or F; $R_7$ is CH$_2$, $R_8$ is O; $R_9$, $R_{10}$, $R_{11}$, and $R_{12}$ are independently selected from the group consisting of H, F, Cl, Br, I and lower alkyl; $R_{13}$ is alkyl, aralkyl or aryl; $R_{14}$ is C-alkyl, C-aralkyl or C-aryl; and $R_{15}$ is lower alkyl;

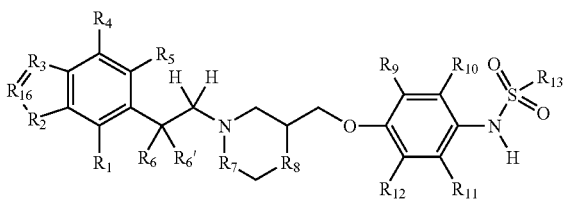

wherein $R_1$, $R_4$ and $R_5$ are independently selected from the group consisting of H, F, Cl, Br, I and OR where R is lower alkyl; $R_2$ is O, S, NH or NR$_{15}$; $R_3$ is N; $R_6$ and $R_6'$ are independently H or F; $R_7$ is CH$_2$; $R_8$ is O; $R_9$, $R_{10}$, $R_{11}$, and $R_{12}$ are independently selected from the group consisting of H, F, Cl, Br, I and lower alkyl; $R_{13}$ is alkyl, aralkyl or aryl; $R_{15}$ is lower alkyl; and $R_{16}$ is C-alkyl, C-aralkyl or C-aryl;

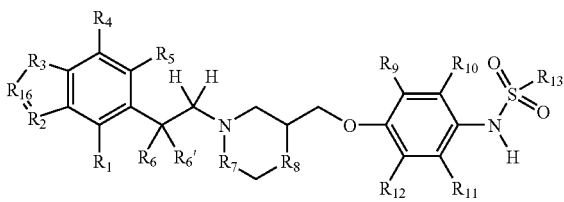

wherein $R_1$, $R_4$ and $R_5$ are independently selected from the group consisting of H, F, Cl, Br, I and OR where R is lower alkyl; $R_2$ is N; $R_3$ is O, S, NH or NR$_{15}$; $R_6$ and $R_6'$ are independently H or F; $R_7$ is CH$_2$, $R_8$ is O, $R_9$, $R_{10}$, $R_{11}$, and $R_{12}$ are independently selected from the group consisting of H, F, Cl, Br, I and lower alkyl, $R_{13}$ is alkyl, aralkyl or aryl; $R_{15}$ is lower alkyl; and $R_{16}$ is C-alkyl, C-aralkyl or C-aryl;

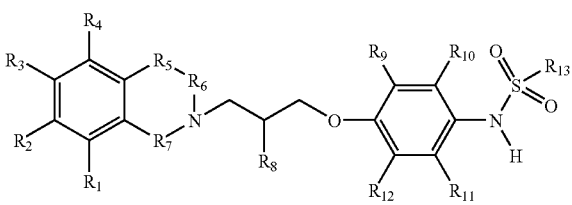

wherein R₁ and R₄ are independently selected from the group consisting of H, F, Cl, Br, I and OR₁₄; R₂ and R₃ are independently selected from the group consisting of F, Cl, Br, I, and OR₁₄, and R₂ and R₃ taken together are O—CH₂—O; R₅, R₆ and R₇ are independently CH₂, CHR₁₅ or C(R₁₅)₂; R₈ is OH, OR, where R is lower alkyl, or F; R₉, R₁₀, R₁₁ and R₁₂ are independently selected from the group consisting of H, F, Cl, Br, I or lower alkyl; R₁₃ is alkyl, aralkyl or aryl; and R₁₄ is C-alkyl, C-aralkyl or C-aryl;

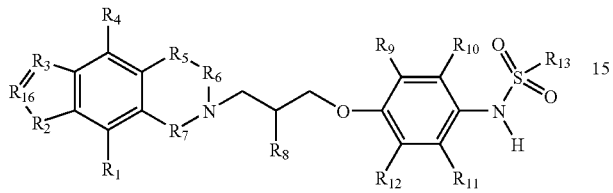

wherein R₁ and R₄ are independently selected from the group consisting of H, F, Cl, Br, I and O R₁₄; R₂ is selected from the group consisting of O, S, NH or NR₁₅; R₃ is N; R₅, R₆ and R₇ are independently CH₂, CHR₁₅ or C(R₁₅)₂; R₈ is OH, OR, where R is lower alkyl, or F; R₉, R₁₀, R₁₁, and R₁₂ are independently selected from the group consisting of H, F, Cl, Br, I and lower alkyl, R₁₃ is alkyl, aralkyl or aryl; R₁₄ is C-alkyl, C-aralkyl or C-aryl; R₁₅ is lower alkyl; and R₁₆ is C-alkyl, C-aralkyl, or C-aryl;

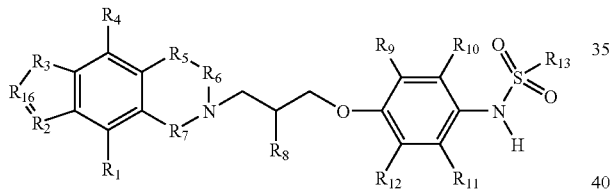

wherein R₁ and R₄ are independently selected from the group consisting of H, F, Cl, Br, I and OR₁₄; R₂ is N; R₃ is selected from the group consisting of O, S, NH and NR₁₅; R₅, R₆ and R₇ are independently CH₂, CHR₁₅ or C(R₁₅)₂; R₈ is OH, OR, where R is lower alkyl, or F; R₉, R₁₀, R₁₁, and R₁₂ are independently selected from the group consisting of H, F, Cl, Br, I and lower alkyl, R₁₃ is alkyl, aralkyl or aryl; R₁₄ is C-alkyl, C-aralkyl or C-aryl; R₁₅ is lower alkyl; and R₁₆ is C-alkyl, C-aralkyl, or C-aryl;

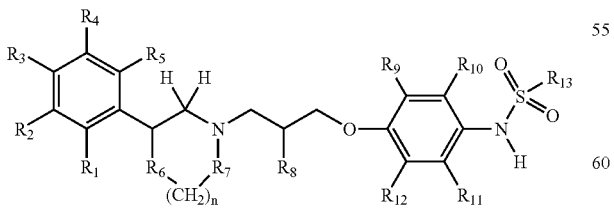

wherein R₁, R₂, R₃, R₄ and R₅ are independently selected from the group consisting of H, F, Cl, Br, I and OR₁₄, and where R₂ and R₃ taken together are O—CH₂—O; R₆ and R₇ are independently CH₂, CHR₁₅ or C(R₁₅)₂, R₈ is OH, OR, where R is lower alkyl, or F; R₉, R₁₀, R₁₁, and R₁₂ are independently selected from the group consisting of H, F, Cl, Br, I and lower alkyl, R₁₃ is alkyl, aralkyl or aryl; R₁₄ is C-alkyl, C-aralkyl or C-aryl, and R₁₅ is lower alkyl; and n=1-3;

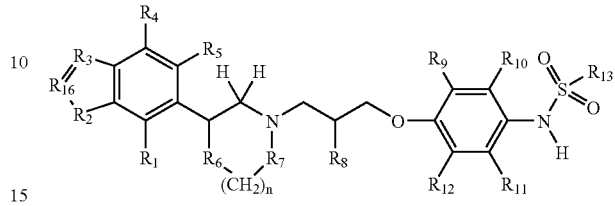

wherein R₁, R₄ and R₅ are independently selected form the group consisting of H, F, Cl, Br, I and OR where R is lower alkyl; R₂ is O, S, NH or NR₁₅; R₃ is N; R₆ and R₇ are independently CH₂, CHR₁₅ or C(R₁₅)₂; R₈ is OH, OR, where R is lower alkyl, or F; R₉, R₁₀, R₁₁, and R₁₂ are independently selected from the group consisting of H, F, Cl, Br, I and lower alkyl, R₁₃ is alkyl, aralkyl or aryl; R₁₅ is lower alkyl; R₁₆ is C-alkyl, C-aralkyl or C-aryl; and n=1-3;

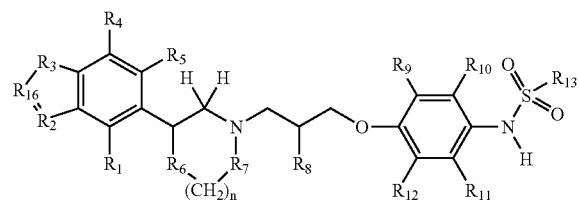

wherein R₁, R₄ and R₅ are independently selected from the group consisting of H, F, Cl, Br, I and OR where R is lower alkyl; R₂ is N; R₃ is O, S, NH or NR₁₅; R₆ and R₇ are independently CH₂, CHR₁₅ or C(R₁₅)₂; R₈ is OH, OR, where R is lower alkyl, or F; R₉, R₁₀, R₁₁, and R₁₂ are independently selected from the group consisting of H, F, Cl, Br, I and lower alkyl, R₁₃ is alkyl, aralkyl or aryl; R₁₅ is lower alkyl; R₁₆ is C-alkyl, C-aralkyl or C-aryl; and n=1-3;

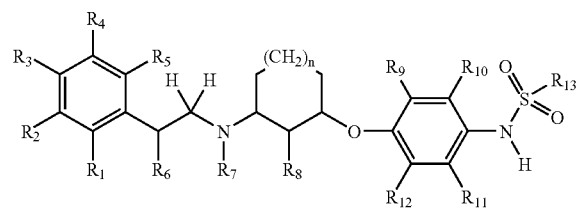

wherein R₁, R₂, R₃, R₄ and R₅ are independently selected from the group consisting of H, F, Cl, Br, I and OR where R is lower alkyl, and where R₂ and R₃ taken together are O—CH₂—O; R₆ and R₇ are independently CH₂, CHR₁₅ or C(R₁₅)₂, R₈ is OH, OR, where R is lower alkyl, or F; R₉, R₁₀, R₁₁, and R₁₂ are independently selected from the group consisting of H, F, Cl, Br, I or lower alkyl, R₁₃ is alkyl, aralkyl or aryl; R₁₅ is lower alkyl; and n=1-3;

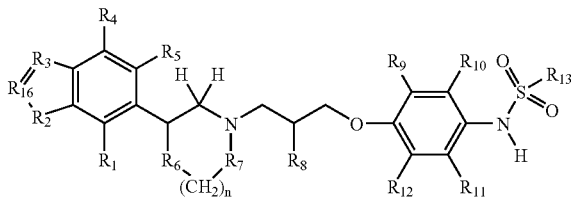

wherein $R_1$, $R_4$ and $R_5$ are independently selected form the group consisting of H, F, Cl, Br, I and OR where R is lower alkyl; $R_2$ is O, S, NH or $NR_{15}$; $R_3$ is N; $R_6$ and $R_7$ are independently $CH_2$, $CHR_{15}$ or $C(R_{15})_2$; $R_8$ is OH, OR, where R is lower alkyl, or F; $R_9$, $R_{10}$, $R_{11}$, and $R_{12}$ are independently selected from the group consisting of H, F, Cl, Br, I and lower alkyl, $R_{13}$ is alkyl, aralkyl or aryl; $R_{15}$ is lower alkyl; $R_{16}$ is C-alkyl, C-aralkyl or C-aryl; $R_{16}$ is C-alkyl, C-aralkyl or C-aryl; and n=1-3;

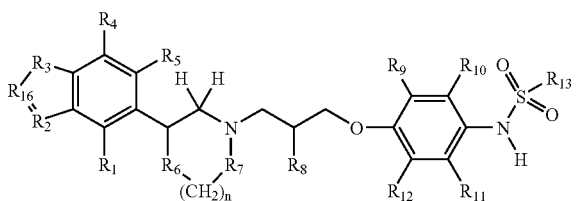

wherein $R_1$, $R_4$ and $R_5$ are independently selected form the group consisting of H, F, Cl, Br, I and or where R is lower alkyl; $R_2$ is N; $R_3$ is O, S, NH or $NR_{15}$; $R_6$ and $R_7$ are independently $CH_2$, $CHR_{15}$ or $C(R_{15})_2$; $R_8$ is OH, OR, where R is lower alkyl, or F; $R_9$, $R_{10}$, $R_{11}$, and $R_{12}$ are independently selected from the group consisting of H, F, Cl, Br, I and lower alkyl, $R_{13}$ is alkyl, aralkyl or aryl; $R_{15}$ is lower alkyl; $R_{16}$ is C-alkyl, C-aralkyl or C-aryl, and n=1-3;

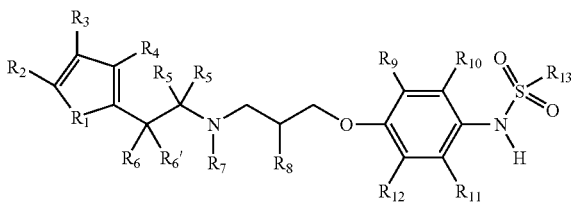

wherein $R_1$ is selected from the group consisting of O, S, NH and $NR_{15}$; $R_2$, $R_3$ and $R_4$ are independently selected from the group consisting of H, F, Cl, Br, I and OR where R is lower alkyl; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$, is OH, OR, where R is lower alkyl, or F; $R_9$, $R_{10}$, $R_{11}$ and $R_{12}$ are independently selected from the group consisting of H, F, Cl, Br, I and lower alkyl; $R_{13}$ is alkyl, aralkyl or aryl; and $R_{15}$ is lower alkyl;

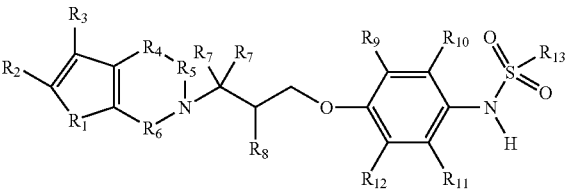

wherein $R_1$ is selected from the group consisting of O, S, NH and $NR_{15}$; $R_2$ and $R_3$ are independently selected from the group consisting of H, F, Cl, Br, I and OR where R is lower alkyl, and $R_2$ and $R_3$ taken together are O—$CH_2$—O; $R_4$, $R_5$ and $R_6$ are independently $CH_2$, $CHR_{15}$ or $C(R_{15})_2$; $R_7$ is H, $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

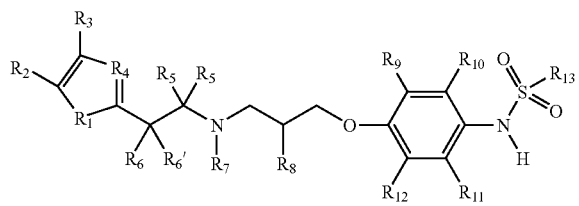

wherein $R_1$ is selected from the group consisting of O, S, NH and $NR_{15}$; $R_2$ and $R_3$ are independently selected from the group consisting of H, F, Cl, Br, I and OR where R is lower alkyl, and $R_2$ and $R_3$ taken together are O—$CH_2$—O; $R_4$ is N; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

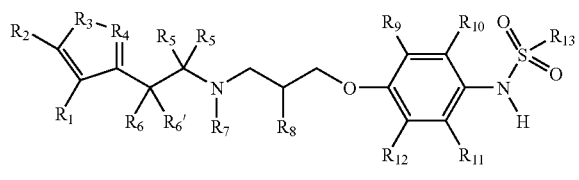

wherein $R_1$ and $R_2$ are independently selected from the group consisting of H, F, Cl, Br, I and OR where R is lower alkyl; $R_3$ is selected from the group consisting of O, S, NH and $NR_{15}$; $R_4$ is N; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$ and $R_{12}$ are independently selected from the group consisting of H, F, Cl, Br, I and lower alkyl; $R_{13}$ is alkyl, aralkyl or aryl; and $R_{15}$ is lower alkyl;

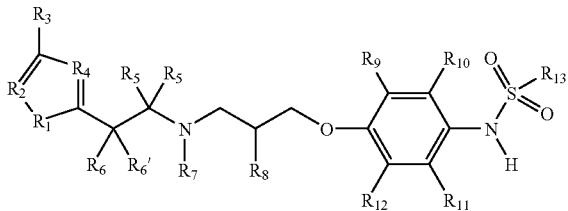

wherein $R_1$ is selected from the group consisting of O, S, NH and NR15; $R_2$ is N; $R_3$ and $R_4$ are is selected from the group consisting of H, F, Cl, Br, I and OR where R is lower alkyl; $R_5$ is H, $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

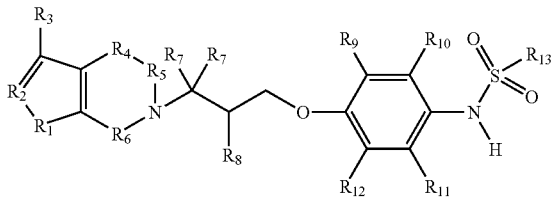

wherein $R_1$ is selected from the group consisting of O, S, NH and $NR_{15}$; $R_2$ is N; $R_3$ is selected from the group consisting of H, F, Cl, Br, I and OR where R is lower alkyl; $R_4$, $R_5$ and $R_6$ are independently $CH_2$, $CHR_{15}$ or $C(R_{15})_2$; $R_7$ is H; $R_8$ is OH, OR, where R is lower alkyl, or F; $R_9$, $R_{10}$, $R_{11}$ and $R_{12}$ are independently selected from the group consisting of H, F, Cl, Br, I or lower alkyl; $R_{13}$ is alkyl, aralkyl or aryl; and $R_{15}$ is lower alkyl;

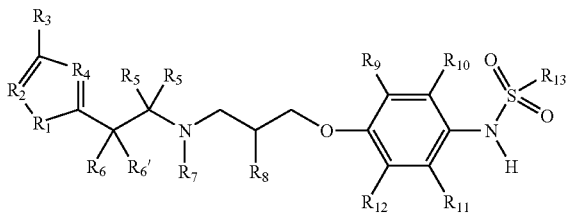

wherein $R_1$ is selected from the group consisting of O, S, NH and $NR_{15}$; $R_3$ is selected from the group consisting of H, F, Cl, Br, I and OR where R is lower alkyl; $R_2$ and $R_4$ are N; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

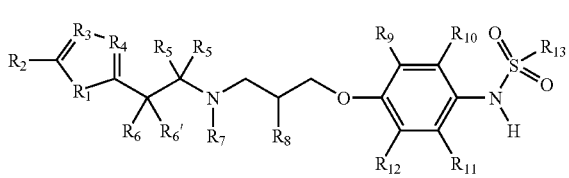

wherein $R_1$ is selected from the group consisting of O, S, NH and $NR_{15}$; $R_2$ is selected from the group consisting of H, F, Cl, Br, I and Or where R is lower alkyl; $R_3$ and $R_4$ are N; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

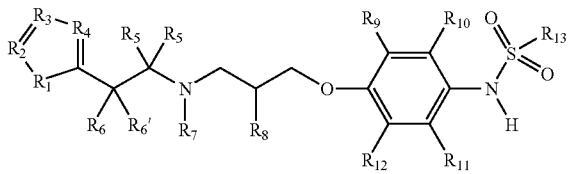

wherein $R_1$ is selected from a group consisting of O, S, NH or $NR_{15}$; $R_2$, $R_3$ and $R_4$ are N; $R_5$ is H, $R_6$ and $R_6'$ are independently H or F; $R_7$ is selected from the group consisting of H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

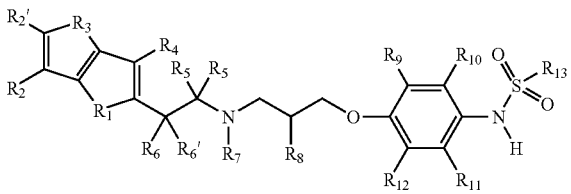

wherein $R_1$ and $R_3$ are independently selected from the group consisting of O, S, NH and $NR_{15}$; $R_2$, $R_2'$ and $R_4$ are independently selected from the group consisting of H, F, Cl, Br, I and OR where R is lower alkyl; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I or lower alkyl; $R_{13}$ is alkyl, aralkyl or aryl; and $R_{15}$ is lower alkyl;

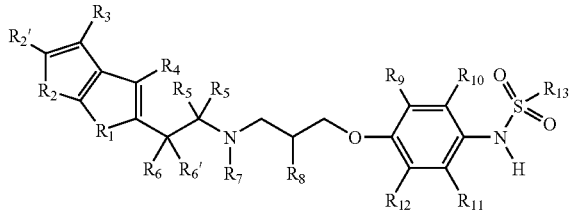

wherein $R_1$ and $R_2$ are independently selected from the group consisting of O, S, NH and $NR_{15}$; $R_2'$, $R_3$ and $R_4$ are independently selected from the group consisting of H, F, Cl, Br, I and OR where R is lower alkyl; $R_5$ is H; $R_6$ and $R_6'$ are independently H or F; $R_7$ is H, lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; and $R_{15}$ is lower alkyl;

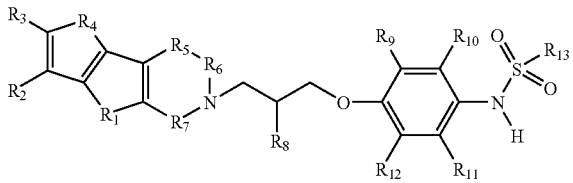

wherein $R_1$ and $R_4$ are independently selected from the group consisting of O, S, NH and $NR_{15}$; $R_2$ and $R_3$ are independently selected from the group consisting of H, F, Cl, Br, I and OR where $R_{14}$, and $R_2$ and $R_3$ taken together are O—$CH_2$—O; $R_5$, $R_6$ and $R_7$ are independently $CH_2$, $CHR_{15}$ or $C(R_{15})_2$; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; $R_{14}$ is C-alkyl, C-aralkyl or C-aryl and $R_{15}$ is lower alkyl;

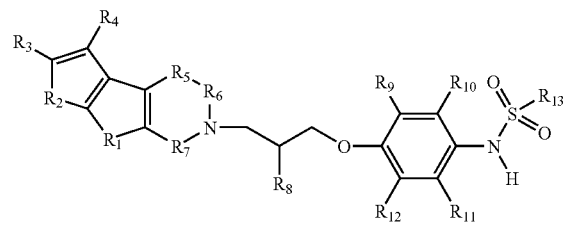

wherein $R_1$ and $R_2$ are independently selected from the group consisting of O, S, NH and $NR_{15}$; $R_2'$, $R_3$ and $R_4$ are independently selected from the group consisting of H, F, Cl, Br, I and $OR_{14}$, and $R_3$ and $R_4$ taken together are O—$CH_2$—O; $R_5$, $R_6$ and $R_7$ are independently $CH_2$, $CHR_{15}$ or $C(R_{15})_2$; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; $R_{14}$ is C-alkyl, C-aralkyl or C-aryl, and $R_{15}$ is lower alkyl;

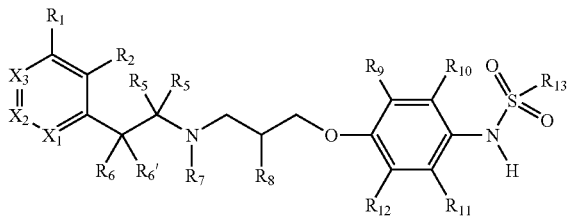

wherein $R_1$, $R_2$, $R_3$ and $R_4$ are independently selected from the group consisting of H, F, Cl, Br, I and OR where R is lower alkyl; and where $R_1$ and $R_2$ taken together are O—$CH_2$—O; $R_5$ is H, $R_6$ and $R_6'$ are independently H or F; $R_7$ is H or lower alkyl, $CH_2Ar$, $CH_2CH_2Ar$, $CH_2CHFAr$ or $CH_2CF_2Ar$, where Ar is aryl, 2-fluorophenyl, 3-fluorophenyl, 4-fluorophenyl, 2,6-difluorophenyl, 2,3,4-trifluorophenyl, or 2,3,4,5,6-pentafluorophenyl; $R_8$ is OH, OR, where R is lower alkyl, or F; $R_9$, $R_{10}$, $R_{11}$, and $R_{12}$ are independently selected from the group consisting of H, F, Cl, Br, I and lower alkyl; $R_{13}$ is alkyl, aralkyl or aryl; $R_{15}$ is lower alkyl; and $X_1$ is C—$R_3$ or N; $X_2$ is C—$R_4$ or N; and $X_3$ is C—$R_4'$ or N;

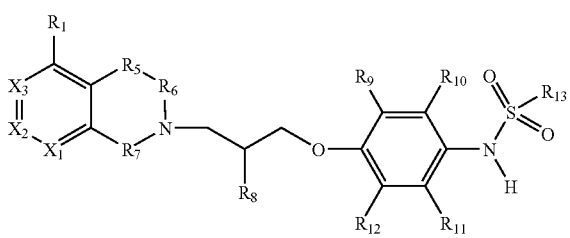

wherein $R_1$, $R_2$, $R_3$ and $R_4$ are independently selected from the group consisting of H, F, Cl, Br, I and $OR_{14}$, and where $R_1$ and R2 taken together are O—$CH_2$—O; $R_5$, $R_6$ and $R_7$ are independently $CH_2$, $CHR_{15}$ or $C(R_{15})_2$; $R_8$ is OH, OR, where R is lower alkyl, or F; $R_9$, $R_{10}$, $R_{11}$, and $R_{12}$ are independently selected from the group consisting of H, F, Cl, Br, I or lower alkyl; $R_{13}$ is alkyl, aralkyl or aryl; $R_{14}$ is C-alkyl, C-aralkyl or C-aryl; $R_{15}$ is lower alkyl; and $X_1$ is C—$R_2$ or N; $X_2$ is C—$R_3$ or N; and $X_3$ is C—$R_4$ or N.

Derivatives of the above compounds in which 5-membered rings contain O, S or N heteroatoms and 6-membered rings contain N heteroatoms are also provided herein. (R)- and (S)-forms, and racemic mixtures thereof, of the foregoing compounds are also provided herein.

Other preferred compounds are those selected from the group consisting of the (S) or (R) forms and racemic mixtures of:

1-(4-methanesulphonamidepheoxy)3-(N-methyl-3,4-dichlorophenylethylamino)-2-propanol;

1-(4-Methanesulphonamidephenoxy)-3-(3,4-dichlorophenylethyl-amino)-2-propanol;

1-(4-Methanesulphonamidephenoxy)-3-(N-ethyl-3,4-dichloro-phenylethylamino)-2-propanol;

1-(4-Methanesulphonamidephenoxy)3-(N-propyl-3,4-dichloro-phenylethylamino)-2-propanol;
1-(4-Methanesulphonamidephenoxy)-3-(N-butyl-3,4-dichloro-phenylethylamino)-2-propanol;
1-(4-Methanesulphonamidephenoxy)-3-(N-benzyl-3,4-dichloro-phenylethylamino)-2-propanol;
1-(4-Methanesulphonamidephenoxy)-3-(N-(2-fluorobenzyl)-3,4-dichlorophenylethylamino)-2-propanol;
1-(4-Methanesulphonamidephenoxy)-3-(N-(3-fluorobenzyl)-3,4-dichlorophenylethylamino)-2-propanol;
1-(4-Methanesulphonamidephenoxy)-3-(N-(3-fluorobenzyl)-3,4-dichloro-phenylethylamino)-2-propanol;
1-(4-Methanesulphonamidephenoxy)-3-(N-(2,6-difluorobenzyl)-3,4-dichloro-phenylethylamino)-2-propanol;
1-(4-Methanesulphonamidephenoxy)-3-(N-(2,3,4-trifluorobenzyl)-3,4-dichlorophenyl-ethylamino)-2-propanol;
1-(4-Methanesulphonamidephenoxy)-3-(N-(2,3,4,5,6-pentafluoro-benzyl)-3,4-dichlor ophenylethylamino)-2-propanol;
1-(4-Methanesulphonamidephenoxy)-3-(N-(2-hydroxyethyl)-3,4-dichloro-phenylethyl-amino)-2-propanol;
1-(3-Methanesulphonamidephenoxy)3-(3,4-dichlorophenylethyl-amino)-2-propanol;
1-(2-Methanesulphonamidephenoxy)-3-(3,4-dichlorophenyl-ethylamino)-2-propanol;
1-(4-Methanesulphonamidophenoxy)-3-(N-acetyl-3,4-dichloro-phenylethylamino)-2-propyl acetate;
N-(3,4-dichlorophenyl)ethyl-5-(4-methanesulphonamidophenoxy)methyl-oxazolidine-2-one;
1-(4-N-methyl-methanesulphonamidephenoxy)-3-(3,4-dichloro-phenylethylamino)-2-propanol;
1-(4-benzenesulphonamidophenoxy)-3-(3,4-dichloro-phenylethyl-amino)-2-propanol;
1-(4-Nitrophenoxy)3-(3,4-dichlorophenylethylamino)-2-propanol;
mixtures thereof and pharmaceutically acceptable salts thereof.

This invention also provides a method of treating neurodegeneration associated with a pathological condition characterized by lowered brain-tissue pH, said method comprising administering to a patient in need of such treatment a pharmaceutically effective amount of a compound having enhanced NMDA receptor blocking activity at said lowered brain-tissue pH over normal brain-tissue pH, said compound being selected from the group consisting of the above-described compounds.

The methods of this invention also include treating neurodegeneration associated with a pathological condition characterized by lowered brain-tissue pH, said method comprising administering to a patient in need of such treatment a pharmaceutically effective amount of a compound having enhanced NMDA receptor blocking activity at said lowered brain-tissue pH over normal brain-tissue pH, said compound being selected from the group consisting of: zolantidine dimaleate; 2-(4-chloroanilino)-4-(4-phenylpiperazino)cyclopent-2-en-1-one; haloperidol; cirazoline; 1,10-phenanthroline; 6-[2-(4-imidazolyl)ethylamino]-N-(4-trifluoromethylphenyl)heptanecarboxamide; (R,S)1-(4-methanesulfonamidophenoxy)-3-(N-methyl-3,4-dichlorophenylethylamine)-2-propanol hydrochloride (AM92016, compound 93); 3-[[4-(4-chlorophenyl)piperazin-1-yl]methyl]-1H-pyrrolo[2,3-b]pyridine; 8-[2-(1,4-benzodiaxan-2-ylmethylamino)ethyl]-8-azaspiro[4.5]decane-7,9-dione; (±)-8-hydroxy-2-dipropylaminotetralin hydrobromide; (±)-7-hydroxy-2-dipropylaminotetralin hydrobromide; 8-[3-(4-fluorophenoxy)propyl]-1-phenyl-1,3,8-triazospiro[4.5]-decan-4-one (AMI 193); PPHT; 4-(4-fluorobenzoyl)-1-(4-phenylbutyl)piperidine; 2-(2-benzofuranyl)-2-imidazoline hydrochloride (2-BFI); benextramine; trifluoperidol; clobenpropit; and benoxathian.

This invention also provides a method of treating neurodegeneration associated with a pathological condition characterized by lowered brain-tissue pH, said method comprising administering to a patient in need of such treatment a pharmaceutically effective amount of a compound having enhanced NMDA receptor blocking activity at said lowered brain-tissue pH over normal brain-tissue pH, said compound being selected from the group consisting of (R)- or (S)-enantiomers or mixtures thereof of compounds of the formula:

A-B-

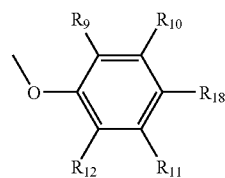

wherein one of $R_9$, $R_{10}$, $R_{11}$, $R_{12}$ and $R_{18}$ is

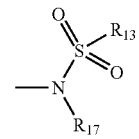

where $R_{13}$ is alkyl, aralkyl or aryl; where $R_{17}$ is H or lower alkyl; and
the others of $R_9$, $R_{10}$, $R_{11}$, $R_{12}$ and $R_{18}$ are H, F, Cl, I or R wherein R is lower alkyl;
or:

A-B-

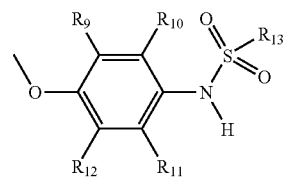

wherein $R_9$, $R_{10}$, $R_{11}$, and $R_{12}$ are independently selected from the group consisting of H, F, Cl, Br, I, and R wherein R is lower alkyl, and $R_{13}$ is alkyl aralkyl or aryl;
wherein A is a bulky, ring-containing group;
and wherein B is selected from the group consisting of:

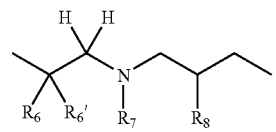

wherein $R_6$ and $R_6'$ are independently H or F; and $R_7$ is H, lower n-alkyl, $CH_2Ar$, $CH_2CH_2Ar$, $CH_2CHFAr$, or $CH_2CHF_2Ar$; and $R_8$ is OH, OR, where R is lower alkyl, or F;

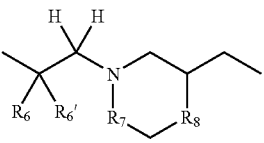

wherein $R_6$ and $R_6'$ are independently H or F; $R_7$ is $CH_2$ and $R_8$ is O;

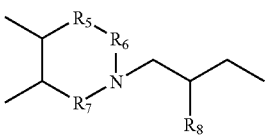

wherein $R_5$, $R_6$ and $R_7$ are independently $CH_2$, CHR or $CR_2$ where R is lower alkyl; and $R_8$ is OH, OR, where R is lower alkyl, or F;

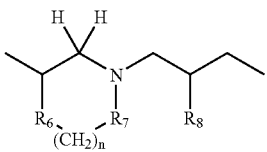

wherein $R_6$ and $R_7$ are independently $CH_2$, CHR or $CR_2$ where R is lower alkyl; and $R_8$ is OH, OR, where R is lower alkyl, or F;

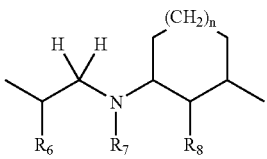

wherein $R_6$ and $R_7$ are independently $CH_2$, CHR or $CR_2$ where R is lower alkyl; $R_8$ is OH, OR, where R is lower alkyl, or F; and n=1-3; and pharmaceutically acceptable salts, enantiomers, enantiomeric mixtures, and mixtures of the foregoing.

The novel compounds disclosed herein may be used to treat pathological conditions not involving lowered brain-tissue pH, as well as pathological conditions involved lowered pH. Such conditions include Parkinson's Disease, Alzheimers, and Amyotrophic Lateral Sclerosis (ALS).

This invention also provides methods of making compounds described herein comprising:

the (S)- or (R)-form of a compound having the formula:

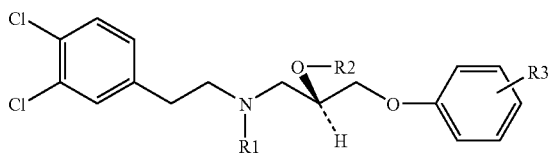

wherein $R_1$ is $CH_3$ or H, $R_2$ is H, and $R_3$ is selected from the group consisting of $NHSO_2CH_3$, $N(CH_3)SO_2CH_3$, $NHSO_2Ph$ and $NO_2$, said method comprising reacting an (S) or (R)-glycidyl (R)—$R_3$-phenyl ether with N-methyl-3,4-dichlorophenylethylamine to form the compound wherein $R_1$ is $CH_3$; or with 3,4-dichlorophenylethylamine to form the compound of the above formula wherein $R_1$ is H.

This invention also comprises a method of forming a further compound of said formula wherein $R_1$ is selected from the group consisting of $C_2H_5$, $C3H_7$, $C_4H_9$, benzyl, 2-fluorobenzyl, 3-fluorobenzyl, 4-fluorobenzyl, 2,6-difluorobenzyl, and 2,3,4-trifluorobenzyl, said method comprising reacting the product of the foregoing method wherein $R_1$ is H with 1,2 dichloroethane to form said further compound.

A further method is provided for forming a further compound of said formula wherein $R_1$ is $C_2H_4$—OH, wherein said method further comprises reacting a product of the above formula wherein $R_1$ is H with O-butyryl glycoaldehyde to give a second reaction product; and further reacting said second reaction product with sodium methoxide to form said further compound.

A further method is provided of forming a further compound of said formula wherein $R_1$ is acetyl comprising reacting the compound of the above formula wherein $R_1$ is H with N,N-dimethylaminopyridine and acetic anhydride.

A further method is provided further comprising forming a further compound of said formula wherein $R_1$ and $R_2$ taken together are $CH_2$—O—$CH_2$ comprising reacting the compound of the above formula wherein $R_1$ is H with 1,1'-carbonyldiimidazole and N,N-dimethylaminopyridine in benzene.

R3 may be a meta- or para-substituent in the reaction intermediates and in the final product. Intermediates and corresponding final products may be in the (S)- or (R)- forms.

A method is also provided for making (S)- or (R)-1-(2-methanesulphonamidephenoxy)-3-(3,4-dichlorophenylethylamino)-2-propanol) comprising the steps of:
(a) reacting 2-nitrophenol with (S)- or (R)-glycidyl nosylate to form (S)- or (R)-glycidyl o-nitrophenyl ether;
(b) reacting the product of step (a) with 3,4-dichloropentylethylamine to form (S) or (R)-1-(2-nitrophenyoxy)-3-(3,4-dichlorophenylethylamino)-2-propanol;
(c) reacting the product of step (b) with p-tolune-sulphonic acid and benzaldehyde to form 2-phenyl-3(N-phenylethylamino)-5-(4-nitrophenoxy methyl)oxazolidine;
(d) reacting the product of step (c) with sodium hydroxide to form 2-phenyl-3(N-phenylethylamino)-5-(4-aminophenoxy methyl)oxazolidine; and
(e) reacting the product of step (d) with diisopropylamine and methansulfonylchloride to form 1-(2-methanesulphoneamidephenoxy)-3-(3,4-dichlorophenylethylamino)-2-propanol.

A method is also provided for making (S)- or (R)-1-(4-N-methyl-methanesulphonamidephenoxy)-3-(3,4-dichlorophenylethylamino)-2-propanol comprising:
(a) reacting (S)- or (R)-blycidyl N-methylsulfonyl-p-aminophenyl ether with potassium carbonate and methyl iodide to form (S)- or (R)-glycidyl N-methyl-N-methanesulfonyl-p-aminophenyl ether;
(b) reacting the product of step a) with 3,4-dichlorophenylethylamine to form (S)- or (R)-1-(4-N-methyl-methanesulphonamidephenoxy)-3-(3,4-dichlorophenylethylamino)-2-propanol.

A method is also provided for making (S)- or (R)-(1-(4-benzenesulphonamideophenoxy)-3-(3,4-dichloro-phenylethylamino)-2-propanol comprising reacting (S)- or (R)-glycidyl N-methylsulfonyl-aminophenyl ether with N,N-diisopropyl-N-ethylamine to form (S)- or (R)-glycidyl N-benzenesulfonyl-p-aminophenyl ether, and reacting said ether with 3,4-dichlorophenylethylamine to form said (S)- or (R)-(1-(4-benzenesulphonamideophenoxy)-3-(3,4-dichlorophenylethylamino)-2-propanol.

A method is also provided for making (S)- or (R)-1-(4-nitrophenoxy)3-(3,4-dichlorophenylethylamino)-2-propanol comprising reacting p-nitrophenyl ether with 3,4-dichlrophenylethylamine to form said (S)- or (R)-1-(4-nitrophenoxy)3-(3,4-dichlorophenylethylamino)-2-propanol.

The remaining NMDA-receptor blockers which are derivatives of and related compounds to those described above may be synthesized, as will be appreciated by those of skill in the art, by methods analogous to those described herein.

DETAILED DESCRIPTION

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups include among others methyl, ethyl, n-propyl, and isoprophyl groups. Lower alkyl groups as referred to herein have one to six carbon atoms.

The term "bulky ring-containing group" refers to a group containing 1 or more ring structures which may be aryl rings or cycloalkyl rings.

The term "cycloalkyl" refers to alkyl groups having a hydrocarbon ring, particularly to those having rings of 3 to 7 carbon atoms. Cycloalky groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

Substitution of alkyl groups includes substitution at one or more carbons in the group by moieties containing heteroatoms. Suitable substituents for these groups include but are not limited to OH, SH, $NH_2$, COH, $CO_2H$, ORc, SRc, NRc Rd, CONRc Rd, and halogens, particularly fluorines where Rc and Rd, independently, are alkyl, unsaturated alkyl or aryl groups. Preferred alkyl and unsaturated alkyl groups are lower alkyl, alkenyl or alkynyl groups having from 1 to about 3 carbon atoms.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Para or meta substitution is preferred. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl ($—C_6H_5$), or naphthyl ($—C_{10}H_7$). Suitable substituents for aryl groups include among others alkyl groups, unsaturated alkyl groups, halogens, OH, SH, $NH_2$, COH, $CO_2H$, ORe, SRe, NRe Rf, CONRe Rf, where Re and Rf independently are alkyl, unsaturated alkyl or aryl groups. Preferred substituents are OH, SH, ORe, and SRe where Re is a lower alkyl, i.e. an alkyl group having from 1 to about 3 carbon atoms. Other preferred substituents are halogens, more preferably fluorine, and lower alkyl and unsaturated lower alkyl groups having from 1 to about 3 carbon atoms. Substituents include bridging groups between aromatic rings in the aryl group, such as $—CO_2—$, $—CO—$, $—O—$, $—S—$, $—NH—$, $—CHCH—$ and $—(CH_2)_1—$ where 1 is an integer from 1 to about 5, and particularly $—CH_2—$. Examples of aryl groups having bridging substituents include phenylbenzoate. Substituents also include moieties, such as $—(CH_2)_1—$, $—O—(CH_2)^1—$ or $—OCO—(CH_2)_1—$, where 1 is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated alkyl groups.

The compounds of Formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose starch, magnesium stearate, talc, vegetable oils, gums, polyalkylene-glycols and the like. Carriers which do not consist of water or water and buffer alone are also contemplated in this invention. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances. Thus part of this invention is a pharmaceutical composition comprising a compound of Formula I, in particular a preferred compound as described above, or a pharmaceutically acceptable salt thereof and an inert carrier.

The dosage of the compounds referred to herein can vary within wide limits and will, of course, be fitted to the individual requirements in each particular case. In the case of oral administration the dosage lies in the range of about 0.1 mg per dosage to about 1000 mg per day of a compound of formula I although the upper limit can also be exceeded when this is shown to be indicated. An amount effective to alleviate the neurodegeneration depends on the individual, however alleviation occurs when the condition in question exhibits either symptomatic improvement or improvement according to an accepted assay. For the compounds herein having enhanced activity at pH lower than normal, dosages of these compounds for use in the methods of this invention involving administration to a patient having lower-than-normal brain-tissue pH, are less than normal dosage amounts for similar compounds not having such enhanced activity at lowered pH. When used to treat stroke or other traumatic ischemic events, the treatment should be administered prior or to or immediately after the event.

Lowered pH due to pathological conditions is between about 6.4 and about 7.2, generally about 6.9. Normal brain-tissue pH is between about 7.2 and about 7.6, generally about 7.4.

EXAMPLES

The following examples illustrate the present invention in more detail. However, they are not intended to limit its scope in any manner.

Example 1

NMDA Receptor Block in Xenopus Oocytes by Novel Compounds

Current recordings were obtained using two electrode voltage clamp of *Xenopus* oocytes injected with cRNA encoding the NR1-1a and NR2B NMDA receptor subunits. Cells were injected with 5-15 ng of cRNA encoding NR1-1a in combination with a 2-3 fold greater amount of either NR2B cRNA. Injected oocytes were maintained at 17° C. in Barths solution containing penicillin (10 U/ml) and streptomycin (10 μg/ml) for 2-6 days, after which recordings were made at room temperature from oocytes continuously perfused in a standard frog Ringers solution. This solution was composed of (in mM): 90 NaCl, 1.0 KCl, 10 Hepes and 0.5 $BaCl_2$. Recording pipettes were filled with 0.3M KCl. Saturating concentrations of glutamate (20-50 μM) and glycine (20 μM) were used to activate the receptor. Drugs were prepared daily from frozen stock solutions in DMSO. Glutamate/glycine-activated currents were typically elicited from a holding potential of −20 to −40 mV. Current signals were digitized and analyzed using custom acquisition software. To study the effects of pH, oocytes were perfused with Ringer's solution at the desired pH until a stable baseline had been reached before subsequent agonist application.

Application of glutamate and glycine produced a stable, rapidly-rising and nondesensitizing current in the majority of oocytes. Oocytes in which the glutamate/glycine current was not stable or in which the baseline holding current drifted were discarded. Inhibition of the glutamate/glycine current by drugs was examined by applying 1-4 different concentrations of the antagonist to each oocyte. The amplitude of the glutamate/glycine current at each concentration of antagonist was expressed as a percentage of the control glutamate/glycine current in the absence of antagonist, and IC50's were determined by fitting the logistic equation to the data (n=3-46 oocytes per condition). On average recordings were made from 14 oocytes per condition. The fold potency boost was calculated as the ratio of the experimental IC50 values determined at pH 7.6 and 6.9 (IC50 at pH 7.6/IC50 at pH 6.9).

TABLE A

Novel NMDA receptor inhibitors with potency boosts >5-fold for changes from pH 7.6 to pH 6.9

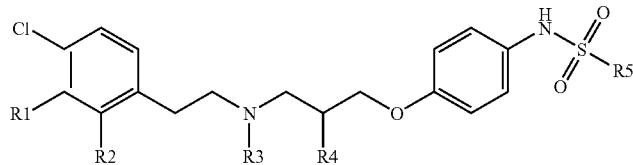

Racemic mixtures were studied when stereochemistry is not indicated. The fold-decrease in IC50 as a function of pH for antagonists of NR1-1a/NR2B receptors was measured in Xenopus oocytes as described above. All compounds were more potent at pH 6.9.

|  | R1 | R2 | R3 | R4 | R5 | IC50 at pH 6.9 (μM) | Fold increase in potency between pH 7.6 and 6.9 |
|---|---|---|---|---|---|---|---|
| Novel Compounds | | | | | | | |
| 93-31 (S) | Cl | H | n-butyl | OH | Me | 0.058 | 51.2 |
| 93-29 (S) | Cl | H | H | OH | phenyl | 1.160 | 18.0 |
| 93-24 | H | Cl | H | OH | Me | 1.360 | 11.8 |
| 93-1 (R) | Cl | H | Methyl | OH | Me | 0.085 | 11.3 |
| 93-8 (S) | Cl | H | EtOH | OH | Me | 0.029 | 11.3 |
| 93-28 (S) | Cl | H | $COCH_3$ | $OCOCH_3$ | Me | 1.638 | 11.1 |
| 93-5 (S) | Cl | H | Ethyl | OH | Me | 0.020 | 8.00 |
| 93-30 (S) | Cl | H | benzyl | OH | Me | 0.070 | 16.8 |
| 93-6 (S) | Cl | H | n-propyl | OH | Me | 0.111 | 6.54 |
| 93-2 (S) | Cl | H | Methyl | OH | Me | 0.063 | 5.87 |

TABLE A-continued

Novel NMDA receptor inhibitors with potency boosts >5-fold for changes from pH 7.6 to pH 6.9

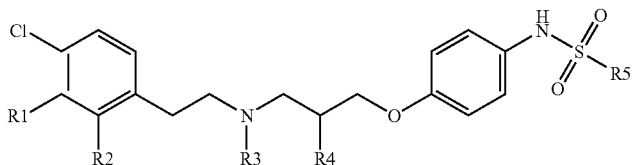

Racemic mixtures were studied when stereochemistry is not indicated. The fold-decrease in IC50 as a function of pH for antagonists of NR1-1a/NR2B receptors was measured in Xenopus oocytes as described above. All compounds were more potent at pH 6.9.

| | R1 | R2 | R3 | R4 | R5 | IC50 at pH 6.9 (μM) | Fold increase in potency between pH 7.6 and 6.9 |
|---|---|---|---|---|---|---|---|
| Known compounds | | | | | | | |
| Haloperidol | — | — | — | — | — | 0.81 | 16.5 |

TABLE B

Novel NMDA receptor inhibitors with pH potency boosts <5 fold for changes from pH 7.6 to pH 6.9

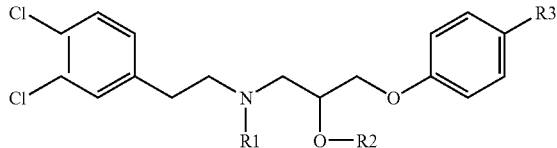

Racemic mixtures were studied when stereochemistry is not indicated. The fold decrease in IC50 as a function of pH for antagonists of NR1-1a/NR2B receptors was measured in Xenopus oocytes as described above.

| | R1 | R2 | R3 | IC50 at pH 6.9 (μM) | Fold increase in potency between pH 7.6 and 6.9 |
|---|---|---|---|---|---|
| Novel compound | | | | | |
| 93-34 (S) | meta-F-benzyl | H | NHSO$_2$Me | 0.210 | 4.62 |
| 93-35 (S) | ortho-F-benzyl | H | NHSO$_2$Me | 0.048 | 3.60 |
| 93-4 (S) | H | H | NHSO$_2$Me | 0.026 | 3.54 |
| 93-3 (R) | H | H | NHSO$_2$Me | 0.099 | 3.26 |
| 93-14 | H | H | OCH$_3$ | 19.900 | 2.01 |
| 93-27 (S) | acetone (C=O with two methyls) | R1 = R2 | NHSO$_2$Me | 0.338 | 0.95 |
| 93-33 (S) | para-F-benzyl | H | NHSO$_2$Me | 0.520 | 0.810 |
| Known compounds | | | | | |
| Ifenprodil | — | — | — | 0.068 | 2.66 |
| Ro256981 | — | — | — | 0.018 | 0.444 |

TABLE C

Importance of chain N ionization on potency boost at low pH for NMDA receptor inhibitors.

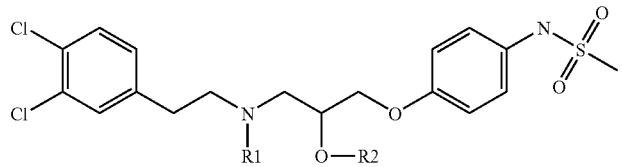

All compounds shown are assumed to be novel. Compounds with pKa values for the chain nitrogen between 9 and 5 undergo changes in the concentration of the ionized species over the range of pH values tested (6.9-7.6). Compounds with reduced pKa values show larger increases in ionization at pH 6.9 compared to pH 7.6. We found a significant correlation (R = −0.98) between the potency boost and pKa of the chain nitrogen for the following series of compounds (n-butyl was omitted because other features of the molecule dominate the potency boost). Molecules with no ionization at this nitrogen showed no pH dependent potency boost. For each compound, the pKa of the amine group in the linker chain was calculated by the web-based pKa calculator from ACDLabs (www.acdlabs.com). The fold decrease in IC50 as a function of pH for antagonist of NR1-1a/NR2B receptors was measured in Xenopus oocytes as described above.

| Compounds with ionization of N changing between pH 6.9 and 7.6 | R1 | R2 | pKa of the chain amine | Fold increase in potency between pH 7.6 and 6.9 |
|---|---|---|---|---|
| 93-4 (S) | H | H | 8.36 | 3.54 |
| 93-6 (S) | n-Propyl | H | 8.11 | 6.54 |
| 93-5 (S) | Ethyl | H | 8.11 | 8.00 |
| 93-31 (S) | n-Butyl | H | 8.11 | 51.2 |
| 93-2 (S) | Me | H | 8.03 | 5.87 |
| 93-8 (S) | EtOH | H | 7.57 | 11.3 |
| 93-30 (S) | Benzyl | H | 7.08 | 16.8 |
| Compound with an unionized nitrogen at both pH 6.9 and 7.6 | | | | |
| 93-27 (S) |  | R1 = R2 | <1 | 0.954 |

TABLE D

Importance of the NHSO$_2$—Me constituent on the phenyl ring for NMDA receptor inhibitors.

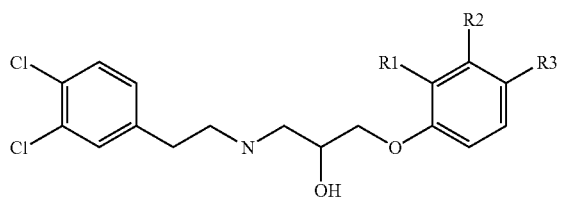

All compounds shown are assumed to be novel. Racemic mixtures were studied when stereochemistry is not indicated. Values not determined are indicated as N.D. The fold decrease in IC50 as a function of pH for antagonists of NR1-1a/NR2B receptors was measured in Xenopus oocytes as described above. All compounds were more potent at pH 6.9.

| Compound | R1 | R2 | R3 | IC50 at pH 6.9 (µM) | Fold increase in potency between pH 7.6 and 6.9 |
|---|---|---|---|---|---|
| 93-4 (S) | H | H | NHSO$_2$—Me | 0.026 | 3.54 |
| 93-9 (S) | H | NHSO$_2$—Me | H | 0.208 | 8.19 |

TABLE D-continued

Importance of the NHSO$_2$—Me constituent on the phenyl ring for NMDA receptor inhibitors.

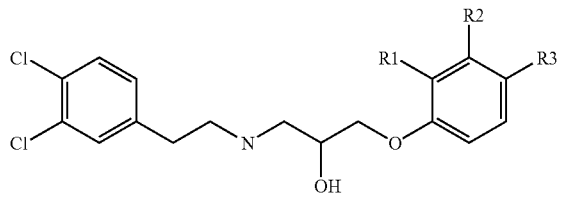

All compounds shown are assumed to be novel. Racemic mixtures were studied when stereochemistry is not indicated. Values not determined are indicated as N.D. The fold decrease in IC50 as a function of pH for antagonists of NR1-1a/NR2B receptors was measured in Xenopus oocytes as described above. All compounds were more potent at pH 6.9.

| Compound | R1 | R2 | R3 | IC50 at pH 6.9 (µM) | Fold increase in potency between pH 7.6 and 6.9 |
|---|---|---|---|---|---|
| 93-32 (S) | NHSO$_2$—Me | H | H | 17.9 | N.D. |
| 93-7 (S) | H | H | N(CH$_3$)SO$_2$—Me | 2.33 | 5.51 |
| 93-29 (S) | H | H | NHSO$_2$-phenyl | 1.16 | 18.02 |
| 93-10 (S) | H | H | NO$_2$ | 12.1 | 1.60 |
| 93-14 | H | H | OCH$_3$ | 19.9 | 2.01 |
| 93-16 | H | H | OCF$_3$ | 11.2 | 4.82 |

TABLE E

Anticonvulsant effect

| Drug | Dose (mg/kg) | Delay from drug injection to electroshock (min) | Control tonic hindlimb extension (THE) time (sec) | THE in drug (% control) |
|---|---|---|---|---|
| Vehicle | 0 | 15 | 8.5 ± 0.3 | 102 ± 3.1 |
| Carbamazepine | 40 | 30 | 8.5 ± 0.3 | 0.0 ± 0.0 |
| 93 | 10 | 15 | 8.5 ± 0.4 | 78.2 ± 4.5 |
| 93 | 10 | 30 | 8.8 ± 0.2 | 58.5 ± 11.3* |
| 93 | 10 | 60 | 9.0 ± 0.2 | 62.4 ± 3.9* |
| 93 | 30 | 240 | 7.4 ± 0.3 | 96.2 ± 1.7 |
| 93-4 | 3 | 15 | 7.2 ± 0.2 | 91.1 ± 2.7 |
| 93-4 | 3 | 60 | 6.7 ± 0.6 | 109 ± 11.5 |
| 93-4 | 30 | 15 | 7.5 ± 0.2 | 66.6 ± 12.5* |
| 93-4 | 30 | 60 | 6.6 ± 0.6 | 30.8 ± 12.1* |
| 93-8 | 30 | 15 | 7.0 ± 0.4 | 91.9 ± 0.4 |
| 93-8 | 30 | 30 | 7.4 ± 0.2 | 85.7 ± 2.8 |
| 93-8 | 30 | 60 | 7.7 ± 0.4 | 59.3 ± 4.1* |
| 93-27 | 30 | 15 | 7.4 ± 0.31 | 97.0 ± 0.6 |
| 93-27 | 30 | 30 | 8.1 ± 0.5 | 95.6 ± 1.3 |
| 93-27 | 30 | 60 | 7.5 ± 0.2 | 89.7 ± 0.8 |

Anticonvulsive effects of (R,S) 1-(4-methanesulfonamidophenoxy)-3-(N-methyl-3,4-dichlorophenylethylamine)-2-propanol hydrochloride (AM92016) [Compound 93], (S)-1-(4-methanesulfonamideophenoxy)-3-(3,4-dichlorophenylethylamine)-2-propanol hydrochloride [Compound 93-4] and (S)-1-(4-methanesulphonamidephenoxy)-e-(N-(2-hydroxyethyl)-3,4-dichlorophenylethylamino)-2-propanol [Compound 93-8], but not (S)-1-(4-methanesulphonamideophenoxy)-3-(N-acetyl-3,4-dichlorophenylethylamino)-2-propyl acetate [compound 93-27] were shown.

Methods: Male Sprague-Dawley rats weighing less than 150 gm were used for these experiments. Maximal electroshock seizures were produced by delivering 200 ms biphasic square-wave pulses of 200 mA at 60 Hz via corneal electrodes, using a Wahlquist Constant Current Source (Salt Lake City, Utah). A drop of 0.9% lidocaine in saline was applied to each cornea 30 s before stimulus delivery to minimize pain. Automatic timers recorded the durations of tonic hindlimb flexion, tonic hindlimb extension (THE), clonus and flaccidity that sequentially followed stimulus delivery. The duration of THE was used as an index of seizure severity. Animals were stimulated on three consecutive days, referred to as "control", "test", and "recovery". A minimum control THE duration of 4 s was used as a criterion for inclusion in subsequent testing; 90% of animals screened had a control THE duration greater than 4 s. On "test" day, each animal received either vehicle or drug at varying intervals prior to stimulation. Reversibility of drug effect on THE was ascertained by response to stimulation administered one day after the "test" session. The values shown in the table are the mean (±sem) THE duration in the test condition, as a percentage of the mean of control and recovery conditions. Four rats were used for each time point.

P<0.001 for difference from vehicle by one-way ANOVA with Dunnett's post hoc test. For all other conditions P>0.05.

Example 2

Synthetic Methods

Compounds implied by the following general formula and given in Table 1 are representative.

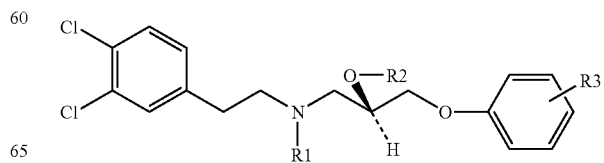

TABLE 1

| Compound | R₁ | R₂ | R₃ |
|---|---|---|---|
| 4 | CH₃ | H | 4-NHSO₂CH₃ |
| 5 | H | H | 4-NHSO₂CH₃ |
| 6 | C₂H₅ | H | 4-NHSO₂CH₃ |
| 7 | C₂H₄—OH | H | 4-NHSO₂CH₃ |
| 8 | C₃H₇ | H | 4-NHSO₂CH₃ |
| 9 | C₄H₉ | H | 4-NHSO₂CH₃ |
| 10 | Benzyl | H | 4-NHSO₂CH₃ |
| 11 | 2-Fluorobenzyl | H | 4-NHSO₂CH₃ |
| 12 | 3-Fluorobenzyl | H | 4-NHSO₂CH₃ |
| 13 | 4-Fluorobenzyl | H | 4-NHSO₂CH₃ |
| 14 | 2,6-Difluorobenzyl | H | 4-NHSO₂CH₃ |
| 15 | 2,3,4-Trifluorobenzyl | H | 4-NHSO₂CH₃ |
| 16 | H | H | 3-NHSO₂CH₃ |
| 17 | H | H | 2-NHSO₂CH₃ |
| 18 | acetyl | acetyl | 4-NHSO₂CH₃ |
| 19 | R₁ = R₂ = (acetone-derived) | | 4-NHSO₂CH₃ |
| 20 | H | H | 4-N(CH₃)SO₂CH₃ |
| 21 | H | H | 4-NHSO₂Ph |
| 22 | H | H | 4-NO₂ |

Synthesis of the above series is exemplified by 4 and 5 as shown in Scheme 1.

Spectroscopic and Purity Determinations. The ¹H-NMR and ¹³C-NMR spectra were recorded on a Varian Inova-400 (400 MHz) spectrometer. HPLC analyses were performed on a Schimadzu LC-10A system equipped with a SPD-10A UV detector. Enantiomeric excesses were determined by HPLC on a Chiralcel OD column using a Hexane-ethanol 90:10 solvent system. Hydrogenations were performed using the baloon technique in a two-necked flask.

Syntheses: All the reactions were performed under anhydrous nitrogen atmosphere in oven-dried glassware.

Preparation of (S)-Glycidyl p-Nitrophenyl Ether (1-S).

p-Nitrophenol (0.92 g, 6.6 mmol) was dissolved in 5 ml anhydrous DMF and cesium fluoride (3.02 g, 19.9 mmol) was added. The reaction mixture was stirred for 1 hour at room temperature and (S)-Glycidyl nosylate (1.71 g, 6.6 mmol) was added. The system was stirred for an additional 24 hours at room temperature. Water (150 ml) was added, and the solution was extracted with ethylacetate. The organic phase was dried over MgSO₄ and evaporated. The residue was purified with column chromatograph using ethylacetate:hexane (50:50) solvent system to give (S)-Glycidyl p-nitrophenyl ether (99.6% ee, based on chiral HPLC with Chiralcel OD, m.p 78-9° C.) as a yellowish solid (1.21 g, 93% yield). The NMR values are the same as the literature values for the racemic mixture: ¹H-NMR (CDCl₃) δ 2.78 (dd, 1H), 2.95 (t 1H), 3.39 (m 1H), 4.0 (dd, 1H), 4.38 (dd, 1H), 6.99 (dd, 2H), 8.2 (dd, 2H).

The (R)-enantiomer of compound 1, starting with (R)-Glycidyl nosylate (1-R) was prepared similarly: ¹H-NMR

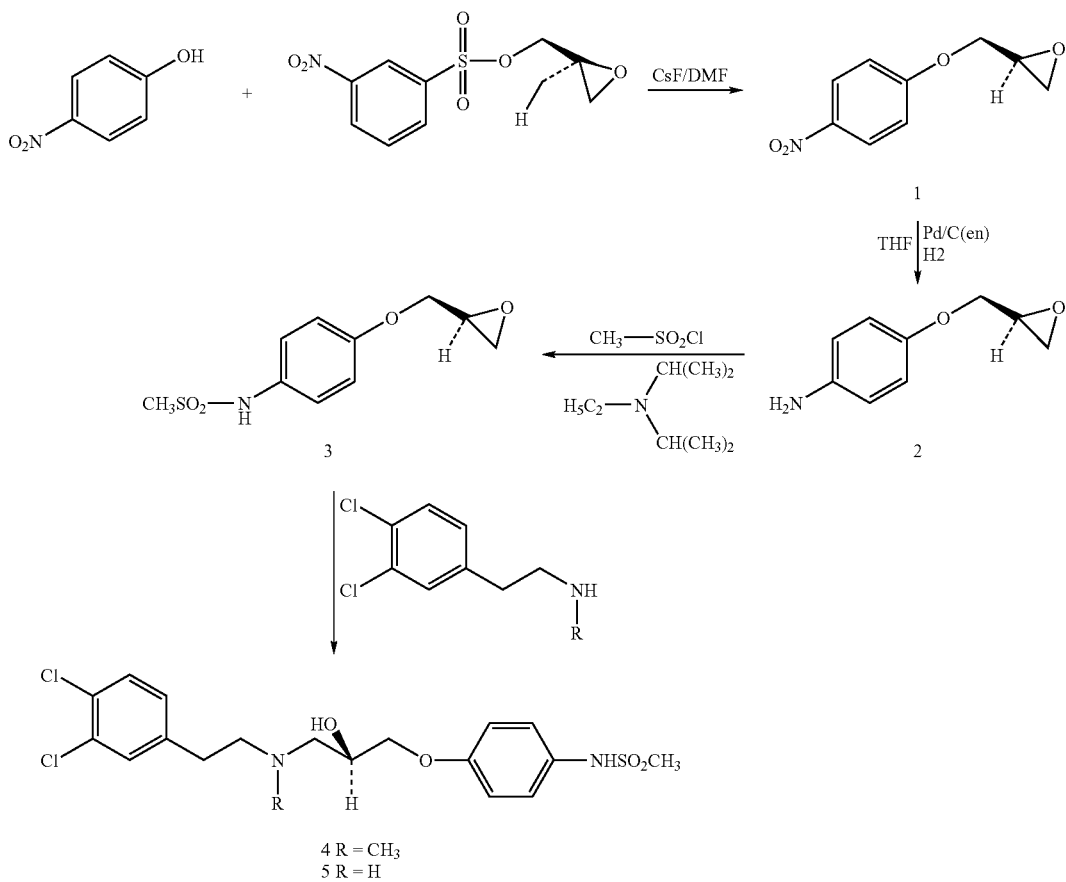

(CDCl$_3$) δ 2.79 (dd, 1H), 2.95 (t 1H), 3.4 (m 1H), 4.0 (dd, 1H), 4.39 (dd, 1H), 7.00 (dd, 2H), 8.2 (dd, 2H).

Preparation of Palladium-On-Carbon Ethylenediamine Complex as a Reducing Agent.

Palladium on activated carbon (5%, w/w, 0.2 g) was tared in a three-necked baloon flask. Then, ethylenediamine (0.42 g, 0.1 M) in 70 ml anhydrous methanol was added to the Pd/C under an argon atmosphere. The reaction mixture was stirred for 32 hours under argon. The catalyst was filtered and washed with methanol and ether, then dried for 24 hours under high vacuum pumpimg.

Preparation of (S)-Glycidyl p-Aminophenyl Ether (2-S.

Compound 1 (0.5 g, 2.6 mmol) and 5% Pd/C(en) (10% of the weight of starting material) in 5 ml anhydrous THF was hydrogenated at ambient pressure and temperature for 3-5 hours. The reaction mixture was filtered through a membrane filter (13, 0.22 μm) and the filtrate was concentrated in vacuo. The compound was obtained as a crude mixture of products arising from nitro group reduction and epoxide ring opening. Isolation of the desired compound was difficult because of the lability of the components of the mixture on silica gel. The product ratio from NO$_2$ reduction and ring opening (94:6) was determined by integrating the epoxide-ring protons in the reduced compound and the methyl proton in the ring opened compound (98% total yield for the mixture). The NMR signals for 2-S are the same as reported in the literature.

$^1$H-NMR (CDCl$_3$) δ 2.69 (dd, 1H), 2.83 (t, 1H), 3.26-3.30 (m 1H), 3.43 (brs, 2H), 3.83 (dd, 1H), 4.1 (dd, 1H), 6.59 (dd, 2H), 6.72 (dd, 2H).

The (R)-enantiomer of compound 2 (2-R) was also prepared from compound 1-R.

$^1$H-NMR (CDCl$_3$) δ 2.69 (dd, 1H), 2.83 (t, 1H), 3.26-3.30 (m 1H), 3.43 (brs, 2H), 3.83 (dd, 1H), 4.1 (dd, 1H), 6.59 (dd, 2H), 6.72 (dd, 2H).

Preparation of (S)-Glycidyl N-Methylsulfonyl-p-Aminophenyl Ether (3-S).

Compound 2-S (0.4 g, 2.4 mmol) dissolved in 20 ml anhydrous DCM and N,N-diisopropyl-N-ethylamine (0.45 ml, 2.6 mmol) were combined at 0° C. After stirring the latter mixture for 15 minutes, methanesulfonyl chloride (0.2 ml, 2.6 mmol) was added dropwise at 0° C. After stirring over night, the reaction was extracted with water and washed with brine. The organic phase was dried over magnesium sulfate and evaporated. The non-volatile residue was purified with flash chromatography using ethyl acetate: DCM (30:70) solvent to give a white solid (m.p: 106-108° C., 70% yield).

$^1$H-NMR (CDCl$_3$) δ 2.77 (dd, 1H), 2.92 (t, 1H), 2.95 (s, 3H), 3.34-3.36 (m 1H), 3.92 (dd, 1H), 4.24 (dd, 1H), 6.34 (s, 1H), 6.91 (dd, 2H), 7.19 (dd, 2H).

The (R)-enantiomer of compound 3 (3-R) was also prepared starting with compound 2-R.

$^1$H-NMR (CDCl$_3$) δ 2.76 (dd, 1H), 2.92 (t, 1H), 2.95 (s, 3H), 3.34-3.36 (m 1H), 3.92 (dd, 1H), 4.24 (dd, 1H), 6.36 (s, 1H), 6.91 (dd, 2H), 7.19 (dd, 2H).

Preparation of (S)-1-(4-Methanesulphonamidephenoxy)3-(N-methyl-3,4-dichloro-phenylethylamino)-2-propanol (4-S).

Compound 3-S (0.326 g, 1.34 mmol) and N-methyl-3,4-dichloropenylethylamine (0.276 g, 1.34 mmol) were dissolved in 5 ml ethanol and refluxed for 20 hours. The solvent was then evaporated and the residue purified by flash chromatography using dichloromethane: methanol (90:10) solvent to give the product as a colorless oil (30% yield).

$^1$H-NMR (CDCl$_3$) δ 2.37 (s, 3H), 2.52-2.78 (m, 6H), 2.93 (s, 3H), 3.91, (dd, Hα, 1H) 3.92 (s, Hβ, !H), 3.98-4.04 (m, 1H), 6.86 (dd, 2H), 7.01 (dd, 1H), 7.17 (dd, 2H), 7.28 (d, 1H), 7.33 (d, 1H).

Compound 4-S was dissolved in ethanol and treated with HCl gas to provide the HCl salt as a white solid which complexes with 1 mol of water. Anal. Calcd for C$_{19}$H$_{24}$N$_2$O$_4$SCl$_2$.HCl.1H$_2$O: C, 45.47; H, 5.42; N, 5.58. Found: C, 43.87; H, 5.41; N, 4.94.

The (R)-enantiomer of compound 4 (4-R) was also prepared from compound 3-R.

$^1$H-NMR (CDCl$_3$) δ 2.37 (s, 3H), 2.52-2.78 (m, 6H), 2.93 (s, 3H), 3.91, (dd, Hα, 1H), 3.92 (s, Hβ, !H), 3.98-4.04 (m, 1H), 6.86 (dd, 2H), 7.01 (dd, 1H), 7.17 (dd, 2H), 7.28 (d, 1H), 7.33 (d, 1H).

Compound 4-R was dissolved in ethanol and treated with HCl gas to provide the HCl salt as a white solid which complexes with 1 mol of water. Anal. Calcd for C$_{19}$H$_{24}$N$_2$O$_4$SCl$_2$.HCl.1H$_2$O: C, 45.47; H, 5.42; N, 5.58. Found: C, 43.80; H, 5.45; N, 5.27.

Preparation of (S)-1-(4-Methanesulphonamidephenoxy)-3-(3,4-dichlorophenylethyl-amino)-2-propanol (5-S).

Compound 3-S (0.364 g, 1.5 mmol) and 3,4-dichlopenylethylamine (0.284 g, 0.11 ml, 1.5 mmol) were dissolved in 5 ml ethanol and refluxed for 5 hours. The solvent was evaporated and the non-volatile residue purified by flash chromatography using dichloromethane: methanol (90:10) solvent to give the product as a colorless oil (80% yield).

$^1$H-NMR (CDCl$_3$) δ 2.75-2.93 (m, 6H), 2.95 (s, 3H), 3.94, (dd, Hα, 1H), 3.96 (s, Hβ, 1H), 4.00-4.05 (m, 1H), 6.86 (dd, 2H), 7.04 (dd, 1H), 7.17 (dd, 2H), 7.30 (d, 1H), 7.35 (d, 1H).

Compound 5-S was dissolved in ethanol and treated with HCl gas to provide the HCl salt as a white solid. Anal. Calcd for C$_{18}$H$_{22}$N$_2$O$_4$SCl$_2$.HCl: C, 46.02; H, 4.93; N, 5.96. Found: C, 46.44; H, 4.95; N, 5.78.

The (R)-enantiomer of compound 5 (5-R) was also prepared from compound 4-R.

$^1$H-NMR (CDCl$_3$) δ 2.75-2.94 (m, 6H), 2.95 (s, 3H), 3.94, (dd, Hα, 1H), 3.96 (s, Hβ, 1H), 3.99-4.05 (m, 1H), 6.87 (dd, 2H), 7.04 (dd, 1H), 7.18 (dd, 2H), 7.30 (d, 1H), 7.35 (d, 1H).

Compound 5-R was dissolved in ethanol and treated with HCl gas to provide the HCl salt as a white solid. Anal. Calcd for C$_{18}$H$_{22}$N$_2$O$_4$SCl$_2$.HCl: C, 46.02; H, 4.93; N, 5.96. Found: C, 46.29; H, 5.06; N, 5.84.

The general reactions for the synthesis of representative compounds 6 and 8-15 are given in Scheme 2. The corresponding substituents are listed in Table 2.

SCHEME 2

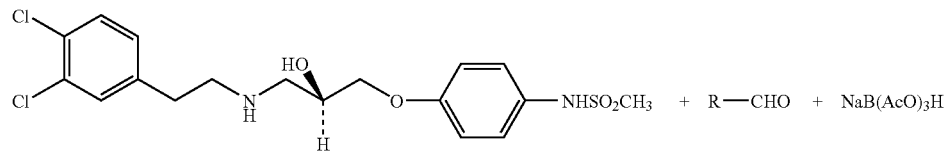

-continued

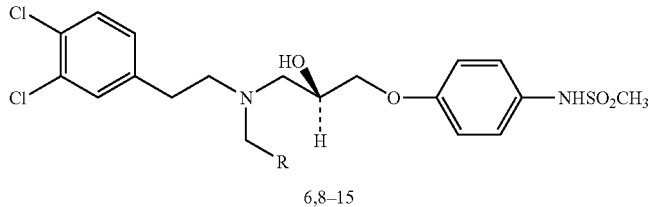

6,8–15

TABLE 2

Substitutents representing both S- and R-enantiomers

| Compound | R |
|---|---|
| 6 | $CH_3$ |
| 8 | $C_2H_5$ |
| 9 | $C_3H_7$ |
| 10 | Phenyl |
| 11 | 2-Fluorophenyl |
| 12 | 3-Fluorophenyl |
| 13 | 4-Fluorophenyl |
| 14 | 2,6-Difluorophenyl |
| 15 | 2,3,4-Trifluorophenyl |

General Method for Preparation of Compounds 6,8-15.

Compound 5 (1 mmol) and the appropriate aldehyde (1 mmol) were dissolved in 10 ml, 1,2-dichloroethane and treated with sodium triacetoxyborohydride (1.4 mmol). After stirring overnight at room temperature, the reaction mixture was quenched with saturated sodium bicarbonate. The water phase was extracted with 1,2-dichloroethane; the organic phase was dried over $MgSO_4$ and evaporated. The residue was purified with flash chromatography to give a colorless oil.

Preparation of (S)-1-(4-Methanesulphonamidephenoxy)-3-(N-ethyl-3,4-dichloro-phenylethylamino)-2-propanol (6-S).

72% yield, solvent for flash chromatography DCM: MeOH (90:10). $^1$H-NMR ($CDCl_3$) δ 1.03 (t, 3H), 2.58-2.80 (m, 8H), 2.91 (s, 3H), 3.88, (dd, Hα, 1H), 3.90 (s, Hβ, 1H), 3.94-3.96 (m, 1H) 6.83 (dd, 2H), 6.99 (dd, 1H), 7.16 (dd, 2H), 7.25 (d, 1H), 7.31 (d, 1H).

Compound 6-S was dissolved in ethanol and treated with HCl gas to provide the HCl salt as a white solid which complexes with 1 mol of water.

Preparation of (S)-1-(4-Methanesulphonamidephenoxy)3-(N-propyl-3,4-dichloro-phenylethylamino)-2-propanol (8-S).

80% yield, solvent for flash chromatography DCM: MeOH (90:10). $^1$H-NMR ($CDCl_3$) δ 0.86 (t, 3H), 1.39-1.56 (m, 2H), 2.56-2.82 (m, 8H), 2.91 (s, 3H), 3.89, (dd, Hα, 1H), 3.90 (s, Hβ, 1H), 3.92-3.96 (m, 1H), 6.84 (dd, 2H), 6.99 (dd, 1H), 7.16 (dd, 2H), 7.25 (d, 1H), 7.31 (d, 1H).

Compound 8-S was dissolved in ethanol and treated with HCl gas to provide the HCl salt as a white solid which complexes with 1 mol of water.

Preparation of (S)-1-(4-Methanesulphonamidephenoxy)-3-(N-butyl-3,4-dichloro-phenylethylamino)-2-propanol (9-S).

74% yield, solvent for flash chromatography DCM: MeOH (90:10). $^1$H-NMR ($CDCl_3$) δ 0.88 (t, 3H), 1.22-1.30 (m, 2H), 1.36-1.45 (m, 2H), 2.44-2.80 (m, 8H), 2.89 (s, 3H), 3.88, (dd, Hα, 1H), 3.89 (s, Hβ, 1H), 3.92-3.96 (m, 1H), 6.82 (dd, 2H), 6.98 (dd, 1H), 7.16 (dd, 2H), 7.24 (d, 1H), 7.29 (d, 1H).

Compound 9-S was dissolved in ethanol and treated with HCl gas to provide the HCl salt as a white solid.

Preparation of (S)-1-(4-Methanesulphonamidephenoxy)-3-(N-benzyl-3,4-dichloro-phenylethylamino)-2-propanol (10-S).

70% yield, solvent for flash chroma-tography DCM: MeOH (90:10). $^1$H-NMR ($CDCl_3$) δ 2.62-2.84 (m, 6H), 2.91 (s, 3H), 3.57 (d, 1H), 3.79 (d, 1H), 3.84, (d, Hα, 1H), 3.86 (s, Hβ, 1H), 3.92-4.08 (m, 1H), 6.80 (dd, 2H), 6.92 (dd, 1H), 7.15 (dd, 2H), 7.19 (d, 1H), 7.24-7.36 (m, 6H).

Compound 10-S was dissolved in ethanol and treated with HCl gas to provide the HCl salt as a white solid which complexes with 1 mol of water.

Preparation of (S)-1-(4-Methanesulphonamidephenoxy)-3-(N-(2-fluorobenzyl)-3,4-dichlorophenylethylamino)-2-propanol (11-S).

65% yield, solvent for flash chro-matography DCM: EtOAc (70:30). $^1$H-NMR ($CDCl_3$) δ 2.69-2.88 (m, 6H), 2.93 (s, 3H), 3.68 (d, 1H), 3.81 (d, 1H), 3.88, (d, Hα, 1H), 3.89 (s, Hβ, 1H), 4.01-4.06 (m, 1H), 6.83 (dd, 2H), 6.91 (dd, 1H), 7.08 (dd, 2H), 7.14-7.20 (m, 3H), 7.22-7.29 (m, 3H).

Compound 11-S was dissolved in ethanol and treated with HCl gas to provide the HCl salt as a white solid which complexes with 1 mol of water.

Preparation of (S)-1-(4-Methanesulphonamidephenoxy)-3-(N-(3-fluorobenzyl)-3,4-dichlorophenylethylamino)-2-propanol (12-S).

85% yield, solvent for flash chro-matography DCM: EtOAc (70:30). $^1$H-NMR ($CDCl_3$) δ 2.69-2.88 (m, 6H), 2.94 (s, 3H), 3.59 (d, 1H), 3.78 (d, 1H), 3.86, (d, Hα, 1H), 3.88 (s, Hβ, 1H), 3.98-4.03 (m, 1H), 6.83 (dd, 2H), 6.93 (dd, 1H), 7.17 (dd, 2H), 7.16-7.21 (m, 3H), 7.24-7.32 (m, 3H).

Compound 12-S was dissolved in ethanol and treated with HCl gas to provide the HCl salt as a white solid which complexes with 1 mol of water.

Preparation of (S)-1-(4-Methanesulphonamidephenoxy)-3-(N-(4-fluorobenzyl)-3,4-dichlorophenylethylamino)-2-propanol (13-S).

80% yield, solvent for flash chro-matography DCM: EtOAc (70:30). $^1$H-NMR ($CDCl_3$) δ 2.67-2.86 (m, 6H), 2.94 (s, 3H), 3.55 (d, 1H), 3.76 (d, 1H), 3.85, (d, Hα, 1H), 3.87 (s, Hβ, 1H), 3.97-4.03 (m, 1H), 6.82 (dd, 2H), 6.92 (dd, 1H), 6.97 (dd, 2H), 7.14-7.20 (m, 5H), 7.29 (d, 1H).

Compound 13-S was dissolved in ethanol and treated with HCl gas to provide the HCl salt as a white solid which complexes with 1 mol of water.

Preparation of (S)-1-(4-Methanesulphonamidephenoxy)-3-(N-(2,6-difluorobenzyl)-3,4-dichlorophenylethylamino)-2-propanol (14-S).

60% yield, solvent system for flash chromatography DCM:EtOAc (70:30). $^1$H-NMR (CDCl$_3$) δ 2.67-2.81 (m, 6H), 2.94 (s, 3H), 3.77 (d, 1H), 3.85 (d, 1H), 3.89, (d, Hα, 1H), 3.90 (s, Hβ, 1H), 4.02-4.09 (m, 1H), 6.85 (dd, 2H), 6.86 (s, 1H), 6.92 (dd, 2H), 7.15 (dd, 2H), 7.17 (d, 1H), 7.25 (dd, 2H).

Compound 14-S was dissolved in ethanol and treated with HCl gas to provide the HCl salt as a white solid.

Preparation of (S)-1-(4-Methanesulphonamidephenoxy)-3-(N-(2,3,4-trifluorobenzyl) -3,4-dichlorophenylethylamino)-2-propanol (15-S).

65% yield, solvent for flash chromatography DCM:EtOAc (70:30). $^1$H-NMR (CDCl$_3$) δ 2.65-2.80 (m, 6H), 2.95 (s, 3H), 3.68 (d, 1H), 3.78 (d, 1H), 3.87, (d, Hα, 1H), 3.89 (s, Hβ, 1H), 4.00-4.04 (m, 1H), 6.83 (dd, 1H), 6.88-6.95 (m, 3H), 7.16 (dd, 2H), 7.18 (dd, 2H), 7.30 (dd, 1H).

Compound 15-S was dissolved in ethanol and treated with HCl gas to provide the HCl salt as a white solid.

Preparation of (S)-1-(4-Methanesulphonamidephenoxy)-3-(N-(2,3,4,5,6-pentafluoro-benzyl)-3,4-dichlorophenylethylamino)-2-propanol (16-S).

40% yield, solvent for flash chromatography DCM:EtOAc (70:30). $^1$H-NMR (CDCl$_3$) δ 2.58-2.79 (m, 6H), 2.93 (s, 3H), 3.41 (dd, 1H), 3.61 (dd, 1H), 4.08(d, 2H), 4.50-4.60 (m, 1H),6.87-6.93 (m, 3H), 7.00(d, 1H), 7.15(d, 1H), 7.19 (dd, 2H).

Compound 7 was prepared in two steps as shown in scheme 3.

Preparation of (S)-1-(4-Methanesulphonamidephenoxy)-3-(N-(2-butyroxyethyl)-3,4-dichlorophenylethylamino)-2-propanol (7a-S).

With the general method, O-Butyryl glycoaldehyde and compound 5 gave the (S)-1-(4-Methanesulphonamidephenoxy)3-(N-(2-butyroxyethyl)-3,4-dichlorophenylethylamino)-2-propanol in 85% yield as a colorless oil. This compound was purified with flash chromatography using DCM: Ethyl acetate (70:30) solvent.

$^1$H-NMR (CDCl$_3$) δ 0.89 (t, 3H), 1.56-1.64 (m, 2H), 2.24 (t, 2H), 2.64-2.87 (m, 6H), 2.90 (s, 3H), 3.87-4.13 (m, 6H), 4.38-4.44 (m, 1H), 6.83 (dd, 2H), 6.99 (dd, 1H), 7.16 (dd, 2H), 7.25 (dd, 1H), 7.31 (d, 1H).

Preparation of (S)-1-(4-Methanesulphonamidephenoxy)-3-(N-(2-hydroxyethyl)-3,4-dichlorophenylethylamino)-2-propanol (7-S).

Reaction of compound 7a-S with sodium methoxide (2 equiv) gave compound 7-S in 75% yield as a colorless oil. This compound was purified with flash chromatography using DCM:MeOH (90:10) solvent.

$^1$H-NMR (CDCl$_3$) δ 2.72-2.86 (m, 8H), 2.94 (s, 3H), 3.64, (dt, 2H), 3.87 (s, Hβ, 1H), 3.89 (dd, Hα, 1H), 3.98-4.04 (m, 1H), 6.84 (dd, 2H), 7.03 (dd, 1H), 7.17 (dd, 2H), 7.29 (d, 1H), 7.33 (d, 1H).

Compound 7-S was dissolved in ethanol and treated with HCl gas to provide the HCl salt as a white solid.

Synthesis of compound 16 is shown in Scheme 4.

SCHEME 3

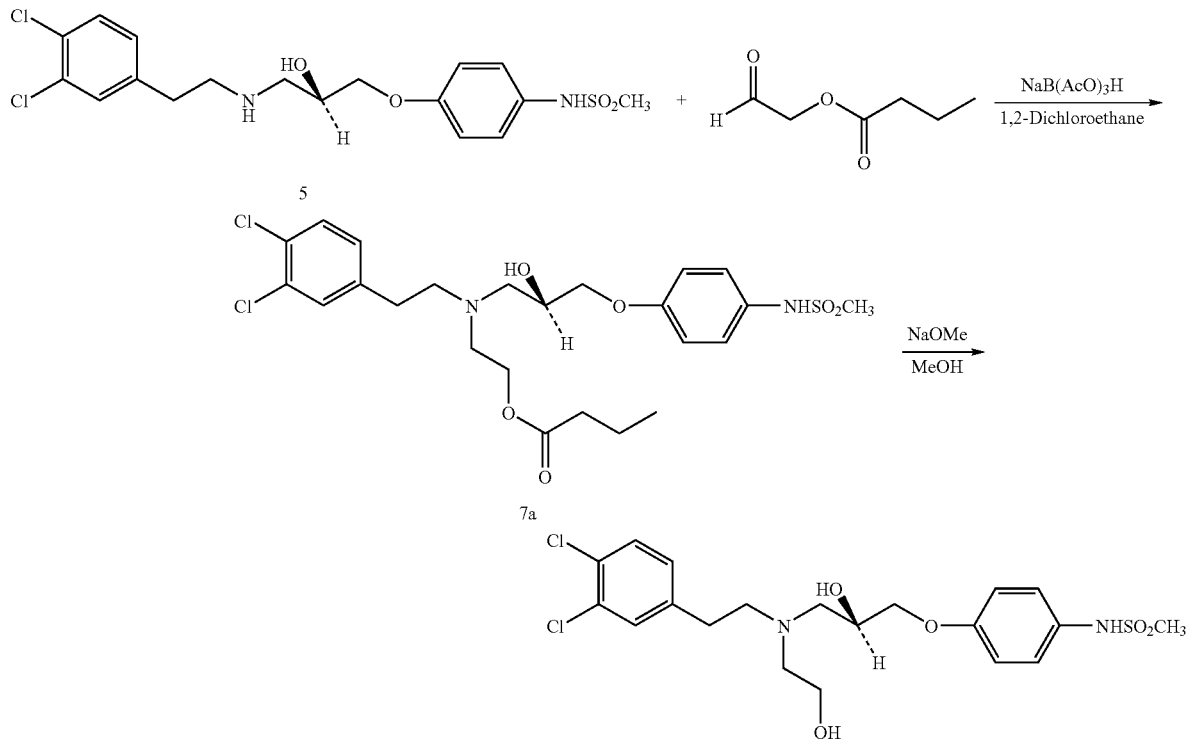

SCHEME 4

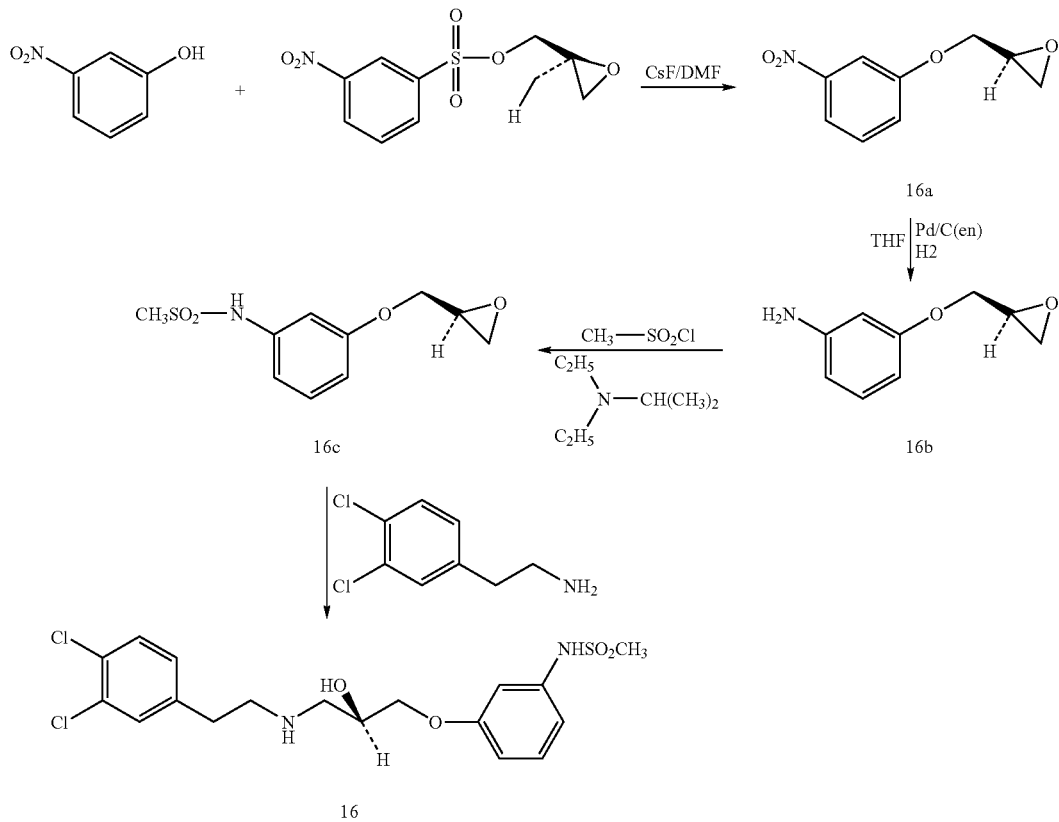

Preparation of (S)-Glycidyl m-Nitrophenyl Ether (16a-S).

3-Nitrophenol (0.92 g, 6.6 mmol) was dissolved in 5 ml anhydrous DMF, and cesium fluoride (3.02 g, 19.9 mmol) was added. The reaction mixture was stirred for 1 hour at room temperature, and (S)-glycidyl nosylate (1.71 g, 6.6 mmol) was added. The reaction mixture was stirred for 20 hours at room temperature. Water (150 ml) was added, and the solution was extracted with ethylacetate. The organic phase was dried over $MgSO_4$ and evaporated. The residue was purified with column chromatograph using ethylacetate: hexane (50:50) solvent to give (S)-glycidyl m-nitrophenyl ether (1.02 g 80% yield, m.p 44-5° C.) as a yellowish solid.

$^1$H-NMR (CDCl$_3$) δ 2.78 (dd, 1H), 2.95 (t 1H), 3.39 (m 1H), 4.0 (dd, 1H), 4.38 (dd, 1H), 7.28 (dd, 1H), 7.41(q, 1H), 7.67-7.87(m, 2H).

Preparation of (S)-Glycidyl m-Aminophenyl Ether (16b-S).

Compound 16a-S (0.5 g, 2.6 mmol) and % 5 Pd/C(en) (10% of the weight of starting material) in 5 ml anhydrous THF was hydrogenated at ambient pressure and temperature for 3-5 hours. The reaction mixture was filtered by using a membrane filter (13, 0.22 μm), and the filtrate was concentrated in vacuo. The resulting compound is a crude mixture of nitro group reduction and epoxide ring opening. Isolation of the desired compound was difficult because of the lability of the components of the mixture on silica gel. The product ratio of the $NO_2$ reduction and ring opening (80:20) was determined on the basis of the integration ratio of the epoxide-ring protons from nitro group reduction and the methyl proton of the ring opened compound (98% total yield for the mixture).

$^1$H-NMR (CDCl$_3$) δ 2.69 (dd, 1H), 2.83 (dt, 1H), 3.27-3.32 (m 1H), 3.43 (brs, 2H), 4.15 (dd, 1H), 4.27 (dd, 1H), 6.13-6.35 (m, 3H), 6.89-7.03 (m, 1H).

Preparation of (S)-Glycidyl N-Methylsulfonyl-m-Aminophenyl Ether (16c-S).

Compound 16b-S (0.4 g, 2.4 mmol) dissolved in 20 ml anhydrous DCM, and N,N-diisopropyl-N-ethylamine (0.45 ml, 2.6 mmol) was added at 0° C. After stirring for 15 minutes, methanesulfonyl chloride (0.2 ml, 2.6 mmol) was added to the reaction mixture at 0° C. After stirring overnight, the reaction mixture was extracted with water and washed with brine. The organic phase was dried and evaporated. The residue was purified with flash chromatography using ethyl acetate:DCM (30:70) solvent to give a colorless oil (45% yield).

$^1$H-NMR (CDCl$_3$) δ 2.75 (dd, 1H), 2.89 (t, 1H), 2.99 (s, 3H), 3.33-3.36 (m 1H), 3.88 (dd, 1H), 4.24 (dd, 1H), 6.70 (dd, 1H), 6.81 (dt, 1H), 7.16-7.23 (m, 2H), 7.52 (s, 1H).

Preparation of (S)-1-(3-Methanesulphonamidephenoxy)3-(3,4-dichlorophenylcthyl-amino)-2-propanol (16-S).

Compound 16c-S (0.364 g, 1.5 mmol) and 3,4-dichloropenylethylamine (0.284 g, 0.11 ml, 1.5 mmol) were dissolved in 5 ml ethanol and refluxed for 10 hours. Then, solvent was evaporated and the residue purified by flash chromatography using dichloromethane: methanol (90:10) solvent to give the product (55% yield).

¹H-NMR (CDCl₃) δ 2.75-2.95 (m, 6H), 3.01 (s, 3H), 3.96, (dd, Hα, 1H), 3.97 (s, Hβ, 1H), 3.99-4.05 (m, 1H), 6.71 (dd, 1H), 6.75 (dd, 1H), 6.82 (t, 1H), 7.05 (dd, 1H), 7.24 (d, 1H), 7.30 (d, 1H), 7.36 (d, 1H).

Compound 16-S was dissolved in ethanol and treated with HCl gas to provide the HCl salt as a white solid.

Compound 17-S was prepared as follows (Scheme 5).

in 25 ml ethanol and refluxed for 12 hours. Then the solvent was evaporated and the residue recrystallized from ethylacetate-petroleum ether to give the product (1.02 g, 99% yield, m.p. 73-74° C.) as a white solid.

¹H-NMR (CDCl₃) δ 2.75-2.94 (m, 6H), 4.02-4.18 (m, 3H), 7.05 (dt, 3H), 7.33 (dd, 2H), 7.53 (dt, 1H), 7.87 (dd, 1H).

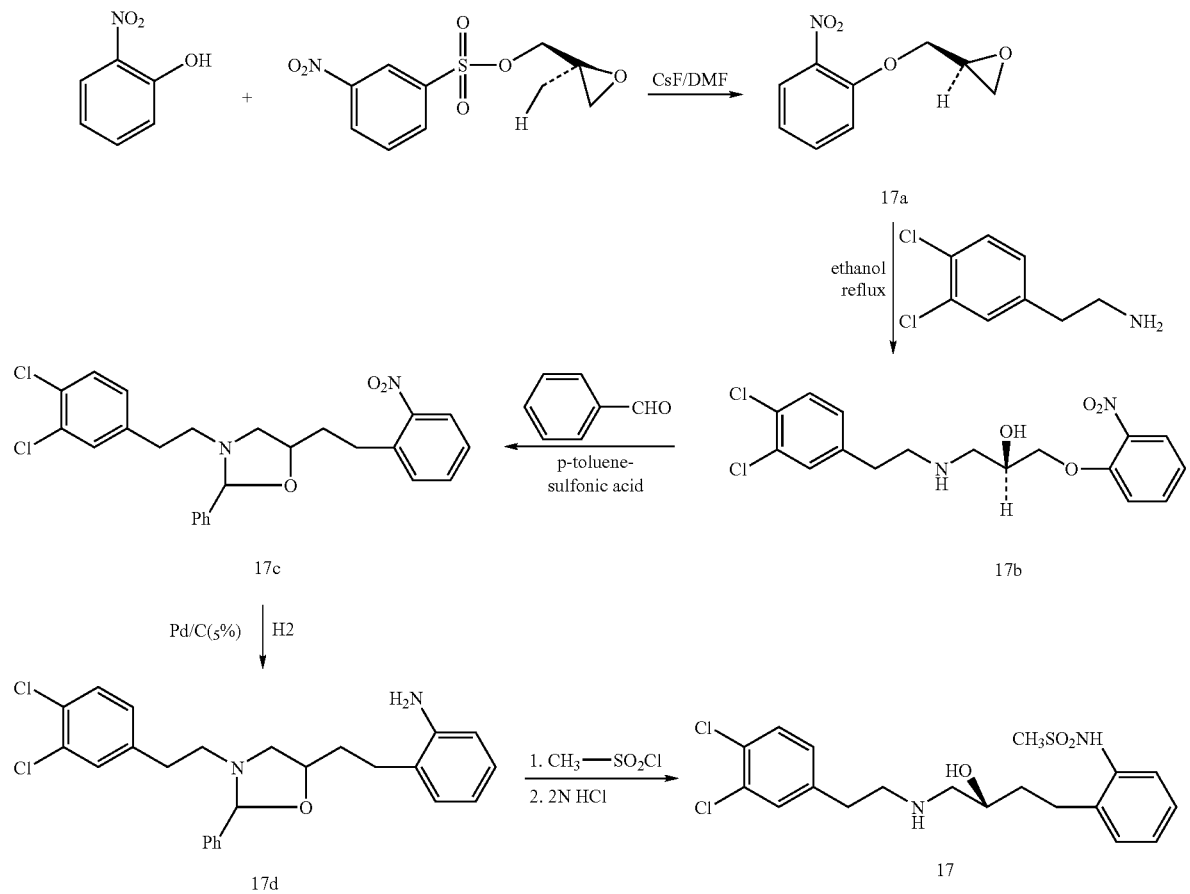

Preparation of (S)-Glycidyl o-Nitrophenyl Ether (17a-S)

2-Nitrophenol (0.92 g, 6.6 mmol) was dissolved in 5 ml anhydrous DMF. Cesium fluoride (3.02 g, 19.9 mmol) was added to the reaction. The reaction mixture was stirred for 1 hour at room temperature and (S)-glycidyl nosylate (1.71 g, 6.6 mmol) was added. The reaction was stirred for 16 hours at room temperature. Water (150 ml) was added, and the solution was extracted with ethylacetate. The organic phase was dried over MgSO₄ and evaporated. The residue was purified with column chromatograph using ethylacetate:hexane (50:50) solvent to give (S)-glycidyl o-nitrophenyl ether (1.21 g, 90% yield, m.p. 46-47° C.) as a white solid.

¹H-NMR (CDCl₃) δ 2.87 (dd, 1H), 2.92 (t 1H), 3.37-3.41 (m 1H), 4.14 (dd, 1H), 4.40 (dd, 1H), 7.06 (dt, 1H), 7.12 (d, 1H), 7.53(dt, 1H), 7.84 (dd, 1H).

Preparation of (S)-1-(2-nitrophenoxy)-3-(3,4-dichlorophenylethylamino)-2-propanol (17b-S).

Compound 17a-S (1.05 g, 5.4 mmol) and 3,4-dichloropenylethylamine (1.02 g, 0.8 ml, 5.4 mmol) were dissolved Preparation of 2-phenyl-3-(N-phenylethylamino)-5-(4-nitrophenoxy methyl)oxazo-lidine(17c-S).

Compound 17b-S (1.02 g, 2.6 mmol), benzaldehyde (0.315 g, 0.3 ml, 2.96 mmol), and p-toluene sulphonic acid (catalytic amount) were dissolved in 50 ml of toluene and refluxed in a Dean Stark apparatus for 30 hours, cooled, and extracted with saturated sodium bicarbonate. The organic layer was dried over MgSO₄ and evaporated yielding a yellow oil as a mixture of stereoisomers. The material was used directly for the next step.

¹H-NMR (CDCl₃) δ 2.61-2.99 (m, 10H), 3.56 (dd, 1H), 3.61 (dd, 1H), 3.83 (t, 1H), 4.03 (t, 1H), 4.20 (dd, 2H), 4.32 (dd, 2H), 4.54-4.58 (m, 1H), 4.64-4.69 (m, 1H), 4.81 (s, 1H), 4.94 (s, 1H), 6.88 (dd, 1H), 6.93 (dd, 1H), 7.04-7.21 (m, 6H), 7.26-7.43 (m, 12H), 7.51 (d, 1H), 7.55 (d, 1H), 7.85 (dd, 1H), 7.88 (dd, 1H).

Preparation of 2-phenyl-3-(N-phenylethylamino)-5-(4-aminophenoxy methyl)oxazo-lidine(17d-S).

Compound 17c-S (1.28 g, 2.7 mmol) was dissolved in 30 ml ethanol. 2N sodium hydroxide(1.28 g) and Pd/C (% 10) (0.128 g, 10% of the weight of starting material) was added to the solution. The reaction was hydrogenated at ambient pressure and temperature for 12 hours. The reaction mixture was filtered by using a membrane filter (13, 0.22 µm), and the filtrate was concentrated in vacuo leaving a yellow oil. The latter was dissolved in DCM and extracted with water, dried over MgSO$_4$ and the solvent removed leaving a colorless oil (0.46 g, 39% yield). The material was used directly in the next step.

Preparation of 1-(2-Methanesulphonamidephenoxy)-3-(3,4-dichlorophenylethylamino)-2-propanol (17-S).

Compound 17d-S (0.460 g, 1.05 mmol) was dissolved in DCM and cooled to 0° C. followed by addition of diisopropylamine (0.149 g, 0.2 ml, 1.15 mmol) and methanesulfonylchloride (0.132 g, 0.1 ml, 1.15 mmol). The reaction mixture was stirred at 0° C. for 2 hours, then warmed to room temperature slowly, and stirred at room temperature for another 16 hours. Solvent was evaporated leaving a yellow brown oil. The latter was added to 50 ml of 1N HCl solution, stirred at room temperature for 4 hours and extracted with DCM. The water layer was removed under reduced pressure, and the resulting solid was recrystallized from ethanol/ether to give the hydrochloride salt of compound 17-S.

$^1$H-NMR (DMSO-d$_6$) δ 2.34 (s, 3H), 2.93-3.39 (m, 6H), 3.94-4.10 (m, 2H), 4.15-4.30 (m, 1H), 6.55-7.03 (m, 2H), 7.24-7.60 (m, 5H), 8.74 (s, 1H).

The syntheses of compounds 18 and 19 are shown in scheme 6.

Preparation of 1-(4-Methanesulphonamidophenoxy)-3-(N-acetyl-3,4-dichloro-phenylethylamino)-2-propyl acetate (18-S).

Compound 5-S (0.303 g, 0.7 mmol) and a catalytic amount of 4-(N,N-dimethylamino) pyridine were dissolved in acetic anhydride (1 ml) and pyridine (1 ml) and stirred at room temperature overnight. The reaction was poured into 10 ml ice-water and extracted with DCM. The organic layer was dried over MgSO$_4$, and evaporated. The residue was purified with flash chromatography using ethyl acetate: DCM (30:70) solvent to give as a colorless oil (75% yield).

$^1$H-NMR (CDCl$_3$) δ 1.96 (s, 3H), 2.08 (s, 3H), 2.82 (dd, 2H), 3.39 (dd, 2H), 3.44 (s, 3H), 3.56 (dd, 2H), 4.07, (dd, Hα, 1H), 4.11 (dd, Hβ, 1H), 5.23-5.35 (m, 1H), 6.96 (d, 2H), 7.03 (dq, 1H), 7.20 (dq, 2H), 7.30 (dd, 1H), 7.37 (dd, 1H).

Compound 18-S was dissolved in ethanol and treated with HCl gas to provide the HCl salt as a white solid.

Preparation of N-(3,4-dichlorophenyl)ethyl-5-(4-methanesulphonamidophenoxy) methyl-oxazolidine-2-one (19-S).

Compound 5-S (0.303 g, 0.7 mmol), 1,1'-carbonyldiimidazole (0.147 g, 0.906 mmol) and a catalytic amount of 4-(N,N-dimethylamino)pyridine were dissolved in 10 ml benzene. After 12 hours refluxing the solvent was evaporated, and the residue was purified with flash chromatography using ethyl acetate:DCM (30:70) solvent to give a colorless oil (85% yield).

$^1$H-NMR (CDCl$_3$) δ 2.88 (t, 2H), 2.95 (s, 3H), 3.42-3.62 (m, 4H), 4.02 (dd, 2H), 4.76-4.82 (m, 1H), 6.51 (s, 1H), 6.83 (dd, 2H), 7.09 (dd, 1H), 7.20 (dd, 2H), 7.32 (d, 1H), 7.35 (d, 1H).

Compound 19-S was dissolved in ethanol and treated with HCl gas to provide the HCl salt as a white solid.

The synthesis of compound 20 is shown in Scheme 7.

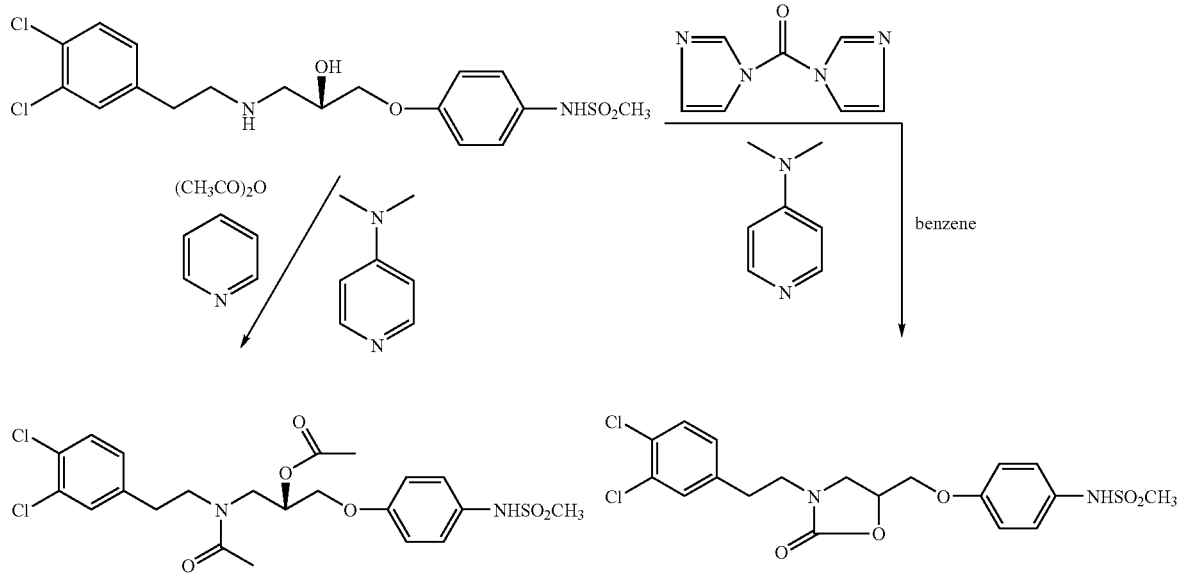

SCHEME 6

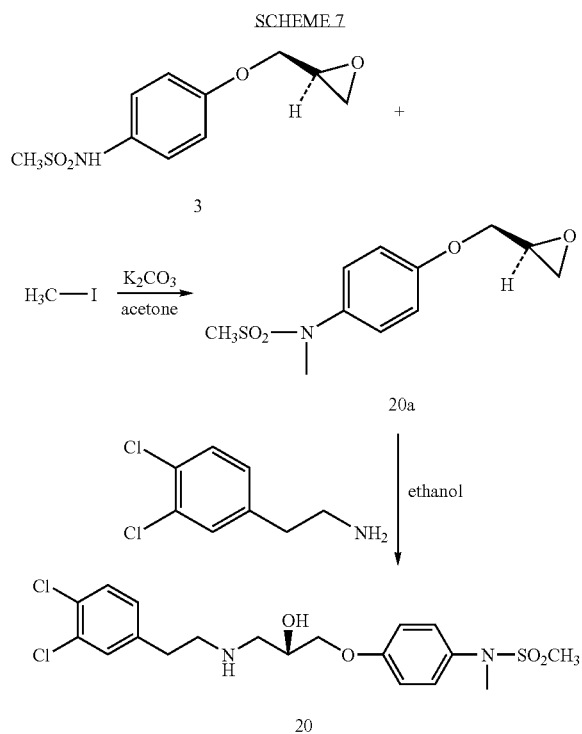

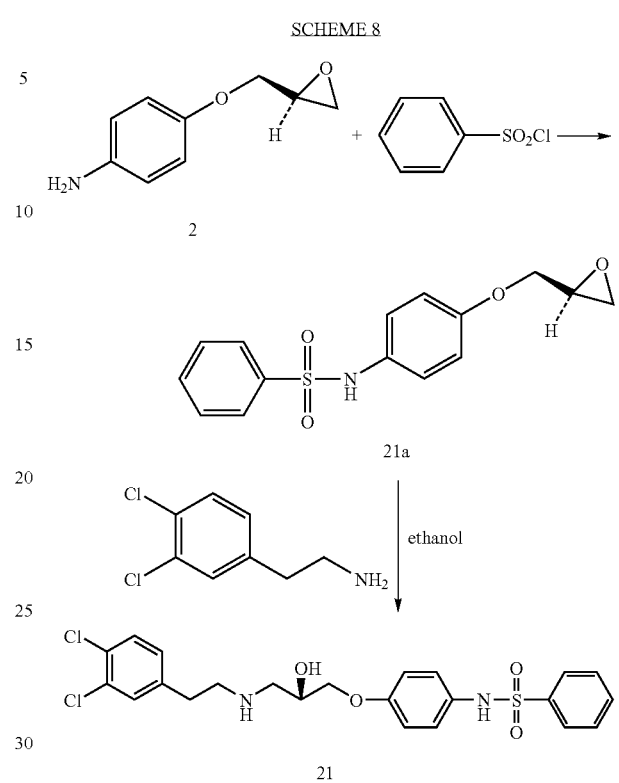

Preparation of (S)-Glycidyl N-methyl-N-Methanesulfonyl-p-Aminophenyl Ether (20a-S).

A solution of compound 3-S (0.243 g, 1 mmol) and potassium carbonate (0.166 g, 1.2 mmol) in 20 ml acetone was stirred for 1 hour at room temperature, then methyl iodide (0.142 g, 0.062 ml, 1 mmol) was added dropwise at room temperature. After stirring for 8 hours, the reaction was filtered and the solvent evaporated to furnish a white solid that was used directly in the next step (0.2 g, 78% yield).

$^1$H-NMR (CDCl$_3$) δ 2.76 (dd, 1H), 2.83 (s, 3H), 2.92 (t, 1H), 3.28 (s, 3H), 3.33-3.39 (m, 1H), 3.93 (dd, 1H), 4.24 (dd, 1H), 6.92 (dd, 2H), 7.29 (dd, 2H).

Preparation of (S)-1-(4-N-methyl-methanesulphonamidephenoxy)-3-(3,4-dichloro-phenylethylamino)-2-propanol (20-S).

Compound 20a-S (0.2 g, 0.8 mmol) and 3,4-dichloropenylethylamine (0.147 g, 0.11 ml, 0.8 mmol) were dissolved in 5 ml ethanol, refluxed for 5 hours, and relieved of solvent by evaporation. The residue was purified by flash chromatography using dichloromethane:methanol (90:10) solvent to give the product as a white solid (80% yield).

$^1$H-NMR (CDCl$_3$) δ 2.72-2.78 (m, 2H), 2.80 (s, 3H), 2.83-2.93 (m, 4H), 3.24 (s, 3H), 3.93, (d, 2H), 4.00-4.04 (m, 1H), 6.85 (dd, 2H), 7.02 (dd, 1H), 7.24 (dd, 2H), 7.26 (d, 1H), 7.31 (d, 1H).

Compound 20-S was dissolved in ethanol and treated with HCl gas to provide the HCl salt as a white solid.

Compound 21 was prepared in a manner similar to compound 5 (Scheme 8)

Preparation of (S)-Glycidyl N-benzenesulfonyl-p-Aminophenyl Ether (21a-S).

Compound 2-S (0.423 g, 2.56 mmol) in 20 ml anhydrous DCM at 0° C. was combined with N,N-diisopropyl-N-ethylamine (0.364 g, 0.49 ml, 2.82 mmol). After stirring for 15 minutes, benzenesulfonyl chloride (0.497 g, 0.36 ml, 2.82 mmol) was added dropwise at 0° C., and the reaction was stirred for 3 hours. The reaction solution was extracted with water and washed with brine; the organic phase dried and evaporated. The residue was purified with flash chromatography using ethyl acetate:DCM (30:70) solvent to give a white solid (75% yield).

$^1$H-NMR (CDCl$_3$) δ 2.74 (dd, 1H), 2.90 (t, 1H), 3.31-3.36 (m 1H), 3.86 (dd, 1H), 4.18 (dd, 1H), 6.66 (s, 1H), 6.77 (dd, 2H), 6.97 (dd, 2H), 7.42 (t, 2H), 7.52 (dd, 1H), 7.70 dd, 2H).

Compound 21a-S (0.620 g, 2.0 mmol) and 3,4-dichloropenylethylamine (0.386 g, 0.30 ml, 2.0 mmol) were dissolved in 25 ml ethanol and refluxed for 16 hours. The solvent was then evaporated and the residue was purified by flash chromatography using dichloromethane: methanol (90:10) solvent to give the product (90% yield).

$^1$H-NMR (CDCl$_3$) δ 2.73-2.94 (m, 6H), 3.89, (dd, Hα, 1H), 3.91 (s, Hβ, 1H), 3.97-4.01 (m, 1H), 6.74 (dd, 2H), 6.94 (dd, 2H), 7.03 (dd, 1H), 7.29 (d, 1H), 7.34 (d, 1d, 1H), 7.43 (t, 2H), 7.52 (dd, 1H), 7.67 (dd, 2H).

Compound 21-S was dissolved in ethanol and treated with HCl gas to provide the HCl salt as a white solid.

The synthesis of compound 22 was accomplished in a single step (Scheme 9).

SCHEME 9

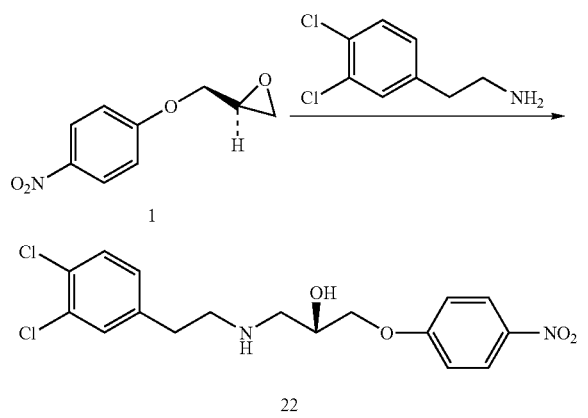

Preparation of (S)-1-(4-Nitrophenoxy)3-(3,4-dichlorophenylethylamino)-2propanol (22-S)

Compound 1-S (0.195 g, 1 mmol) and 3,4-dichloropenylethylamine (0.190 g, 0.15 ml, 1 mmol) were dissolved in 5 ml ethanol and refluxed for 2 hours. After 2 hours, a solid precipitated from the reaction (0.296 g, 77% yield). It proved to be pure by NMR and TLC.

$^1$H-NMR (CDCl$_3$) δ 2.74-2.80 (m, 3H), 2.86-2.97 (m, 3H), 4.02-4.08 (m, 3H), 6.96 (dd, 2H), 7.04 (dd, 1H), 7.31 (d, 1H), 7.36 (d, 1H), 8.20 (dd, 2H).

The invention claimed is:

1. A method of treating neurodegeneration associated with a pathological condition characterized by lowered brain-tissue pH, said method comprising administering to a patient in need of such treatment a pharmaceutically effective amount of a compound having enhanced NMDA receptor blocking activity at said lowered brain-tissue pH over normal brain-tissue pH, said compound being selected from the group consisting of (R)- or (S)-enantiomers and racemic mixtures of a compound of the formula:

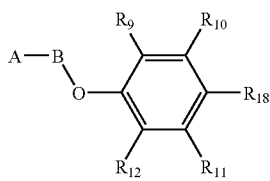

wherein one of $R_9$, $R_{10}$, $R_{11}$, $R_{12}$ and $R_{18}$ is

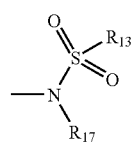

wherein $R_{13}$ is alkyl, aralkyl or aryl; $R_{17}$ is H or lower alkyl; and the others of $R_9$, $R_{10}$, $R_{11}$, $R_{12}$ and $R_{18}$ are H, F, Cl, Br, I or lower alkyl; wherein A is

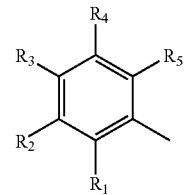

wherein $R_1$ and $R_5$ are independently H or F; $R_2$, $R_3$ and $R_4$ are independently selected from the group consisting of H, F, Cl, Br, I and O(lower alkyl); or $R_2$ and $R_3$ taken together are O—CH$_2$—O;
and B is

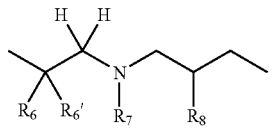

wherein $R_6$ and $R_6'$ are independently H or F; and $R_7$ is CH$_2$Ar, CH$_2$CH$_2$Ar, CH$_2$CHFAr, or CH$_2$CF$_2$Ar, where Ar is 2,3,4,5,6-pentafluorophenyl; and $R_8$ is OH, or O(lower alkyl);
and pharmaceutically acceptable salts, enantiomers, enantiomeric mixtures, and mixtures of the foregoing.

2. A compound selected from the group consisting of (R)- or (S)-enantiomers and racemic mixtures of a compound of the formula:

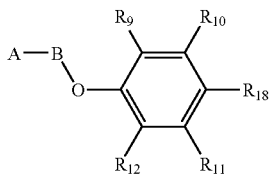

wherein one of $R_9$, $R_{10}$, $R_{11}$, $R_{12}$ and $R_{18}$ is

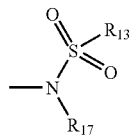

wherein $R_{13}$ is alkyl, aralkyl or aryl; $R_{17}$ is H or lower alkyl; and
the others of $R_9$, $R_{10}$, $R_{11}$, $R_{12}$ and $R_{18}$ are H, F, Cl, Br, I or lower alkyl;
wherein A is

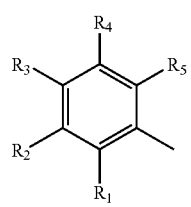

wherein $R_1$ and $R_5$ are independently H or F; $R_2$, $R_3$ and $R_4$ are independently selected from the group consisting of H, F, Cl, Br, I and O(lower alkyl); or $R_2$ and $R_3$ taken together are O—$CH_2$—O;

and B is

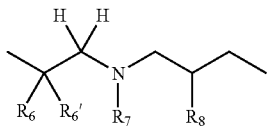

wherein $R_6$ and $R_6'$ are independently H or F; and $R_7$ is $CH_2Ar$, $CH_2CH_2Ar$, $CH_2CHFAr$, or $CH_2CF_2Ar$, where Ar is 2,3,4,5,6-pentafluorophenyl; and $R_8$ is OH, or O(lower alkyl).

3. The compound of claim 2 wherein $R_7$ is $CH_2Ar$, where Ar is 2,3,4,5,6-pentafluorophenyl.

4. The compound of claim 2 wherein $R_8$ is OH.

5. The compound of claim 2 wherein $R_8$ is O(lower alkyl).

6. A pharmaceutical composition comprising a therapeutically effective amount of a compound of claim 2 optionally in a pharmaceutically acceptable carrier.

7. The pharmaceutical composition of claim 6 suitable for oral administration.

8. The pharmaceutical composition of claim 6 suitable for parenteral administration.

* * * * *